(12) United States Patent
Ma et al.

(10) Patent No.: US 11,225,462 B2
(45) Date of Patent: Jan. 18, 2022

(54) CRYSTAL FORMS OF OXYPYRIDINE AMIDE DERIVATIVE AND PREPARATION METHOD THEREFOR

(71) Applicants: JIANGSU HENGRUI MEDICINE CO., LTD., Jiangsu (CN); SHANGHAI HENGRUI PHARMACEUTICAL CO., LTD, Shanghai (CN)

(72) Inventors: Yahui Ma, Jiangsu (CN); Haoyu Zhang, Shanghai (CN); Long Han, Shanghai (CN); Qiyun Shao, Shanghai (CN); Zhenxing Du, Jiangsu (CN); Jie Wang, Jiangsu (CN); Jun Feng, Shanghai (CN); Feng He, Shanghai (CN)

(73) Assignees: JIANGSU HENGRUI MEDICINE CO., LTD., Jiangsu (CN); SHANGHAI HENGRUI PHARMACEUTICAL CO., LTD., Shanghai (CN)

( * ) Notice: Subject to any disclaimer, the term of this patent is extended or adjusted under 35 U.S.C. 154(b) by 0 days.

(21) Appl. No.: 17/257,528

(22) PCT Filed: Jul. 1, 2019

(86) PCT No.: PCT/CN2019/094170
§ 371 (c)(1),
(2) Date: Dec. 31, 2020

(87) PCT Pub. No.: WO2020/007256
PCT Pub. Date: Jan. 9, 2020

(65) Prior Publication Data
US 2021/0122714 A1 Apr. 29, 2021

(30) Foreign Application Priority Data

Jul. 2, 2018 (CN) .......................... 201810710037.1

(51) Int. Cl.
*C07D 211/86* (2006.01)
(52) U.S. Cl.
CPC ........ *C07D 211/86* (2013.01); *C07B 2200/13* (2013.01)
(58) Field of Classification Search
CPC .......................... C07D 211/86; C07B 2200/13
See application file for complete search history.

(56) References Cited

U.S. PATENT DOCUMENTS

| 10,633,375 B2 * | 4/2020 | Yang | .................... C07D 471/04 |
| 2005/0171148 A1 | 8/2005 | Mjalli et al. | |

FOREIGN PATENT DOCUMENTS

| CN | 107793396 | 3/2018 |
|---|---|---|
| WO | WO-96/30396 | 10/1996 |
| WO | WO-99/41276 | 8/1999 |
| WO | WO-2004/002405 | 1/2004 |
| WO | WO-2013/056060 | 4/2013 |
| WO | WO-2013/093484 | 6/2013 |
| WO | WO-2017/005725 | 1/2017 |
| WO | WO-2017/023992 | 2/2017 |
| WO | WO-2018/039094 | 3/2018 |
| WO | WO-2018/041122 | 3/2018 |

OTHER PUBLICATIONS

Asakai, Rei, M.D., Ph.D., et al., "Factor XI Deficiency in Ashkenazi Jews in Israel," The New England Journal of Medicine, 1991, vol. 325, No. 3, pp. 153-158.
Cheng, Qiufang, et al., "A role for factor XIIa-mediated factor XI activation in thrombus formation in vivo," Blood, 2010, vol. 116, No. 19, pp. 3981-3989.
Crosby, Jeffrey R., et al., "Antithrombotic Effect of Antisense Factor XI Oligonucleotide Treatment in Primates," Arterioscler Thromb Vasc Biol, 2013, vol. 33, pp. 1670-1678.
Cushman, Mary, et al., "Coagulation factors IX through XIII and the risk of future venous thrombosis: the Longitudinal Investigation of Thromboembolism Etiology," Blood, 2009, vol. 114, No. 14, pp. 2878-2883.
Eriksson, Bengt I., et al., "Novel Oral Factor Xa and Thrombin Inhibitors in the Management of Thromboembolism," Annu. Rev. Med. 2011, vol. 62, pp. 41-57.
Salomon, Ophira, et al., "Patients with severe factor XI deficiency have a reduced incidence of deep-vein thrombosis," Thromb Haemost, 2011, vol. 105, pp. 269-273.
Salomon, Ophira, et al., "Prevalence, causes, and characterization of factor XI inhibitors in patients with inherited factor XI deficiency," Blood, 2003, vol. 101, No. 12, pp. 4783-4788.
Schumacher, William A., et al., "Inhibition of Factor XIa as a New Approach to Anticoagulation," Arterioscler Thromb Vasc Biol, 2010, vol. 30, pp. 388-392.
International Search Report dated Sep. 20, 2019 issued in International Patent Application No. PCT/CN2019/094170 with English translation, 7 pages.
First Office Action dated May 6, 2020 issued in corresponding Taiwan Patent Application No. 108123123 with English translation, 7 pages.

* cited by examiner

*Primary Examiner* — Timothy R Rozof
(74) *Attorney, Agent, or Firm* — Foley & Lardner LLP

(57) ABSTRACT

The present invention relates to crystal forms of an oxypyridine amide derivative and a preparation method therefor. In particular, the present invention relates to crystal forms A, B, C, D, E and F of a compound represented by formula (I) and a preparation method therefor. The crystal forms of the compound represented by formula (I) as described in the present invention have good crystal form stability and may be better for clinical use.

14 Claims, 25 Drawing Sheets

CRYSTAL FORMS OF OXYPYRIDINE AMIDE DERIVATIVE AND PREPARATION METHOD THEREFOR

CROSS-REFERENCE TO RELATED APPLICATIONS

The present application is a 371 of PCT/CN2019/094170, filed Jul. 1, 2019, which is based upon and claims priority to Chinese patent application CN201810710037.1, filed on Jul. 2, 2018, both of which are hereby incorporated by reference in their entireties.

TECHNICAL FIELD

The present disclosure falls within the field of pharmaceutical chemistry and relates to crystal forms of an inhibitor of blood coagulation factor XIa, (S)-4-(4-(tert-butoxy)-2-(4-(5-chloro-2-propionylphenyl)-5-methoxy-2-oxopyridin-1(2H)-yl)butanamido)benzoic acid and a preparation method therefor.

BACKGROUND 12 million people around the world die each year from cerebrovascular disease, cerebral infarction, myocardial infarction, coronary heart disease, arteriosclerosis and other cardiovascular and cerebrovascular diseases, and account for nearly a quarter of the world's total death. Each year over 2.6 million people die from cardiovascular diseases in China, and 75% of surviving patients are disabled, of which more than 40% are severely disabled. Currently, thrombosis caused by cardiovascular and cerebrovascular diseases and diabetes and complications thereof has become an urgent problem to be solved.

According to data from the independent market analysis agency Datamonitor in 2011, it is predicted that with the production of generic drugs, the share of the drugs for cardiovascular and metabolic diseases in seven major markets will reach a peak in 2011 and then gradually decrease, and the sales amount thereof will fall from $109 billion in 2010 to $101 billion in 2019. The market of the drugs for thrombus remains basically stable, with the sales amount falling from $19.5 billion in 2010 to $18.9 billion in 2019 (Datamonitor: HC00034-001, HC00139-001). It is also shown in the investigation report from Guangzhou Biaodian Medical Information Co., Ltd. in 2011 that the market size of antithrombotic drugs in China in 2011 will reach 8.135 billion yuan, with an increase of 20.52% year-on-year, and has huge market potential (Market Research Report on Antithrombotic Drugs: Guangzhou Biaodian Medical Information Co., Ltd. (2011)).

The process of human blood coagulation which consists of an intrinsic pathway, an extrinsic pathway, and a common pathway (Annu. Rev. Med. 2011. 62:41-57), is a chain reaction in which multiple zymogens are sequentially activated and the process is continuously strengthened and amplified. The coagulation cascade reaction is initiated by the intrinsic pathway (also known as the contact activation pathway) and the extrinsic pathway (also known as the tissue factor pathway) to generate FXa, and then thrombin (FIIa) is generated by the common pathway, which finally leads to fibrin formation.

The intrinsic pathway refers to a process in which factor XII is activated to form a XIa-VIIIa-Ca2±P L complex which then activates factor X, and the extrinsic pathway for coagulation refers to a process from the release of tissue factors (TF) to the formation of a TF-VIIaCa2+ complex and activation of factor X. The common pathway refers to a process in which the two pathways, after the formation of factor Xa, are combined to activate prothrombin and finally to generate fibrin, wherein FXI is necessary to maintain the intrinsic pathway and plays a key role in the amplification process of a coagulation cascade reaction. In the coagulation cascade reaction, thrombin can lead to a feedback activation of FXI, and the activated FXI (FXIa) promotes the production of thrombin in large quantities, thereby amplifying the coagulation cascade reaction. Therefore, the antagonists for FXI have been widely developed for the treatment of various thrombosis.

Traditional anticoagulant drugs, such as warfarin, heparin, low molecular weight heparin (LMWH), and new drugs marketed in recent years such as FXa inhibitors (rivaroxaban, apixaban, etc.) and thrombin inhibitors (dabigatran etexilate, hirudin, etc.), have relatively good effects on reducing thrombosis and due to the significant efficacy thereof, occupy the vast majority of market share in drugs for cardiovascular and cerebrovascular diseases. However, the side effects of traditional anticoagulant drugs are becoming more and more significant, wherein the "bleeding risk" is one of the most serious problems (N Engl J Med 1991; 325:153-8, Blood. 2003; 101:4783-4788).

Human FXI deficiency (FXI activity <15 U/dL), also called hemophilia C, is manifested by mild bleeding phenotype, and spontaneous bleeding only occurs in a minority of patients. The hemostatic function of the patients suffering from this disease is not affected even upon injury or surgery, and hemophilia C patients can get pregnant and give birth normally (Arterioscler Thromb Vasc Biol. 2010; 30:388-392). It can be seen therefrom that the safety of FXIa is significantly better than that of FXa. Therefore, the target FXIa has become a hot topic for major companies and research institutions. Studies have shown that in a thrombosis model, inhibiting FXIa factors can effectively inhibit the formation of thrombus, but in more severe cases of thrombosis, FXIa has little effect (Blood. 2010; 116(19): 3981-3989). It is shown in clinical statistics that increasing the amount of FXIa will increase the prevalence rate of VTE (Blood 2009; 114:2878-2883), and people with severe FXIa deficiency have a reduced risk of suffering from DVT (Thromb Haemost 2011; 105:269-273).

FXIa is used as an emerging target, and patent applications which disclose compounds having a FXIa inhibitory activity include WO 9630396, WO 9941276, WO 2013093484, WO 2004002405, WO 2013056060, WO 2017005725, US 20050171148, WO 2017023992 and WO 2018039094, wherein only the antisense oligonucleotide (ASO) BAY-2306001 from Bayer entered a phase II clinical trial and achieved good results. In the phase I clinical trial of this drug, the FXI activity in subjects showed a sustained, dose-dependent decrease, accompanied with a prolonged aPTT, and no drug-related bleeding symptoms occurred even the FXI in the body reduced to an undetectable level, showing a potential of FXIa as an emerging target (Arterioscler Thromb Vasc Biol, 2013, 33(7)1670-1678). However, FXI ASO must be administered by injection and has a slower onset, which takes several weeks to exert an antithrombotic effect and may be limited when used as a drug for prevention and treatment. In terms of small molecule inhibitors, only FXIa inhibitor BMS-962212 from BMS is currently in a phase II clinical trial. Therefore, the research on new FXIa inhibitors is of great significance.

WO 2018041122 discloses a series of oxopyridine amides FXIa inhibitors, which have been structurally characterized therein and comprise a compound of formula (I). Furthermore, this application also comprises a biological evaluation on the compound of formula (I), which shows that the compound has a significant inhibitory effect on FXIa and a significant anticoagulant effect on human blood, and in addition, it is found that the compound has a good pharmacokinetic absorption, leading to an obvious pharmacokinetic absorption effect, Compound of formula (I)

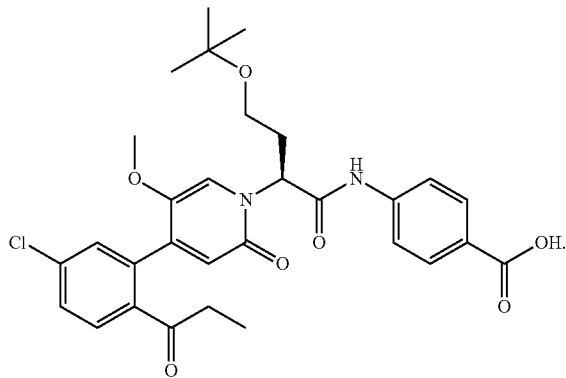

A crystal form acting as a pharmaceutical active ingredient often affects the chemical stability of a drug. Different crystallization conditions and storage conditions may lead to changes in the crystal structure of a compound, sometimes accompanied with the production of other forms of crystal forms. In general, an amorphous drug product has an irregular crystal structure, which often leads to other defects, such as poor product stability, finer crystallization, difficulty in filtration, easy to agglomerate, and poor fluidity. Polymorphism of drugs have different requirements for product storage, production and scale up. Therefore, it is necessary to conduct an in-depth study on crystal forms of the compound of formula (I) to improve various properties thereof.
Content of the Present Invention In order to explore the relationship between specific pharmaceutically acceptable forms and physical and chemical properties of a FXIa inhibitor compound, and to develop a specific pharmaceutically acceptable form that is more suitable as a drug, the present disclosure provides crystal forms of a FXIa inhibitor, (S)-4-(4-(tert-butoxy)-2-(4-(5-chloro-2-propionylphenyl)-5-methoxy-2-oxopyridin-1(2H)-yl)butanamido)benzoic acid (a compound of formula (I)), a preparation method therefor and uses thereof.

The present disclosure provides a crystal form A of the compound of formula (I), wherein the crystal form A has an X-ray powder diffraction pattern comprising characteristic peaks at 2θ values of 7.420, 8.000, 8.642, 12.900 and 22.400, and the error range may be ±0.3, ±0.2 or ±0.1.

Further, the crystal form A has an X-ray powder diffraction pattern comprising characteristic peaks at 2θ values of 7.420, 8.000, 8.642, 12.900, 16.281, 18.280, 20.018, 21.119 and 22.400, and the error range may be ±0.3, ±0.2 or ±0.1.

Further, the crystal form A has an X-ray powder diffraction pattern comprising characteristic peaks at 2θ values of 7.420, 8.000, 8.642, 12.900, 16.281, 18.280, 20.018, 21.119, 22.400 and 24.458, 26.100, and the error range may be ±0.3, ±0.2 or ±0.1.

The present disclosure provides a crystal form B of the compound of formula (I), wherein the crystal form B has an X-ray powder diffraction pattern comprising characteristic peaks at 2θ values of 7.620, 8.680, 11.042, 11.638, 12.339, 16.320 and 19.381, and the error range may be ±0.3, ±0.2 or ±0.1.

Further, the crystal form B has an X-ray powder diffraction pattern comprising characteristic peaks at 2θ values of 7.620, 8.680, 11.042, 11.638, 12.339, 14.461, 16.320, 18.123, 18.381 and 19.381, and the error range may be ±0.3, ±0.2 or ±0.1.

Further, the crystal form B has an X-ray powder diffraction pattern comprising characteristic peaks at 2θ values of 7.620, 8.680, 11.042, 11.638, 12.339, 14.461, 16.320, 18.123, 18.381, 19.381, 22.020, 25.038 and 26.460, and the error range may be ±0.3, ±0.2 or ±0.1.

The present disclosure provides crystal form C of the compound of formula (I), wherein the crystal form C has an X-ray powder diffraction pattern comprising characteristic peaks at 2θ values of 7.283, 8.780, 10.664, 11.264, 14.744, 15.456, 16.587 and 17.598, and the error range may be ±0.3, ±0.2 or ±0.1.

Further, the crystal form C has an X-ray powder diffraction pattern comprising characteristic peaks at 2θ values of 7.283, 8.780, 10.664, 11.264, 14.744, 15.456, 16.587, 17.598, 18.165, 18.915, 20.158, 21.025 and 22.363, and the error range may be ±0.3, ±0.2 or ±0.1.

Further, the crystal form C has an X-ray powder diffraction pattern comprising characteristic peaks at 2θ values of 5.312, 6.704, 7.283, 8.780, 9.544, 10.664, 11.264, 12.335, 14.124, 14.744, 15.456, 16.587, 17.598, 18.165, 18.915, 20.158, 21.025, 22.363, 23.211, 24.504, 24.713, 26.042 and 27.534, and the error range may be ±0.3, ±0.2 or ±0.1.

The present disclosure provides a crystal form D of the compound of formula (I), wherein the crystal form D has an X-ray powder diffraction pattern comprising characteristic peaks at 2θ values of 7.021, 7.901, 8.259, 9.200, 10.639, 12.320, 13.821, 14.180, 14.580, 15.519, 16.120, 16.661, 18.500, 19.919 and 20.600, and the error range may be ±0.3, ±0.2 or ±0.1.

Further, the crystal form D has an X-ray powder diffraction pattern comprising characteristic peaks at 2θ values of 7.021, 7.901, 8.259, 9.200, 10.639, 12.320, 13.821, 14.180, 14.580, 15.519, 16.120, 16.661, 18.500, 19.919, 20.600, 21.320, 21.700, 22.358, 22.820, 23.221, 23.538, 24.241 and 25.060, and the error range may be ±0.3, ±0.2 or ±0.1.

Further, the crystal form D has an X-ray powder diffraction pattern comprising characteristic peaks at 2θ values of 7.021, 7.901, 8.259, 9.200, 10.639, 12.320, 13.821, 14.180, 14.580, 15.519, 16.120, 16.661, 18.500, 19.919, 20.600, 21.320, 21.700, 22.358, 22.820, 23.221, 23.538, 24.241, 25.060, 25.520, 26.920, 27.420, 27.940, 28.720, 29.020, 29.420, 30.560, 31.402, 32.460, 35.380, 35.919 and 37.261, and the error range may be ±0.3, ±0.2 or ±0.1.

The present disclosure provides a crystal form E of the compound of formula (I), wherein the crystal form E has an X-ray powder diffraction pattern comprising characteristic peaks at 2θ values of 6.460, 7.480, 7.977, 16.220, 19.360 and 21.720, and the error range may be ±0.3, ±0.2 or ±0.1.

Further, the crystal form E has an X-ray powder diffraction pattern comprising characteristic peaks at 2θ values of 6.460, 7.480, 7.977, 8.662, 11.299, 12.140, 14.038, 16.220, 17.440, 18.560, 19.360 and 21.720, and the error range may be ±0.3, ±0.2 or ±0.1.

Further, the crystal form E has an X-ray powder diffraction pattern comprising characteristic peaks at 2θ values of 6.460, 7.480, 7.977, 8.662, 11.299, 12.140, 14.038, 16.220, 17.440, 18.560, 19.360, 21.720, 22.664, 24.922, 25.940, 26.840 and 29.620, and the error range may be ±0.3, ±0.2 or ±0.1.

The present disclosure provides a crystal form F of the compound of formula (I), wherein the crystal form F has an X-ray powder diffraction pattern comprising characteristic peaks at 2θ values of 5.761, 9.800, 10.640, 11.621, 14.021, 16.180, 16.460, 17.520, 21.460 and 24.580, and the error range may be ±0.3, ±0.2 or ±0.1.

Further, the crystal form F has an X-ray powder diffraction pattern comprising characteristic peaks at 2θ values of 5.761, 9.800, 10.640, 11.621, 14.021, 16.180, 16.460, 16.740, 17.520, 21.460, 22.820, 23.939, 24.580 and 26.280, and the error range may be ±0.3, ±0.2 or ±0.1.

Further, the crystal form F has an X-ray powder diffraction pattern comprising characteristic peaks at 2θ values of 5.761, 9.800, 10.640, 11.621, 14.021, 16.180, 16.460, 16.740, 17.520, 18.560, 19.142, 19.820, 21.460, 22.820, 23.939, 24.580, 25.981, 26.280, 26.861, 27.700, 28.580, 28.921, 29.480, 30.840, 31.340, 32.801, 33.300, 33.921, 35.321, 36.843, 38.660, 40.101, 41.121 and 41.600, and the error range may be ±0.3, ±0.2 or ±0.1.

The present disclosure also relates to a method for preparing crystal form A, crystal form B, crystal form C, crystal form D, crystal form E and crystal form F of the compound of formula (I) wherein the method comprises taking an amount of the compound of formula (I), adding an appropriate amount of a solvent for crystallization, filtering and drying to obtain crystal form A, crystal form B, crystal form C, crystal form D, crystal form E or crystal form F of the compound of formula (I).

The solvent used for crystallization of crystal form A, crystal form B, crystal form C, crystal form D, crystal form E, and crystal form F of the compound of formula (I) is selected from one or more of a hydrocarbon solvent, an ether solvent, an alcohol solvent, an ester solvent, a ketone solvent, a nitrile solvent, a halogenated hydrocarbon solvent, a nitrogen-containing solvent, water and dimethyl sulfoxide. The hydrocarbon solvent includes, but is not limited to, cyclohexane, n-hexane, n-heptane, toluene, o-xylene or p-xylene; the ether solvent includes, but is not limited to, tetrahydrofuran, diethyl ether, propylene glycol methyl ether, methyl tert-butyl ether, isopropyl ether or 1,4-dioxane; the alcohol solvent includes, but is not limited to, methanol, ethanol, isopropanol, n-propanol, isopentanol or trifluoroethanol; the ester solvent includes, but is not limited to, ethyl acetate, ethyl formate, tert-butyl acetate, ethyl propionate, isopropyl acetate or butyl acetate; the ketone solvent includes, but is not limited to, acetone, acetophenone, 4-methyl-2-pentanone, 2-butanone or methyl isobutyl ketone; the nitrile solvent includes, but is not limited to, acetonitrile or propionitrile; the halogenated hydrocarbon solvent includes, but is not limited to, chloromethane, dichloromethane, 1,2-dichloroethane, chloroform or tetrachloromethane; and the nitrogen-containing solvent includes, but is not limited to, nitromethane, N,N-dimethylformamide or N,N-dimethylacetamide.

The crystallization method of crystal form A, crystal form B, crystal form C, crystal form D, crystal form E, and crystal form F of the compound of formula (I) is selected from a room temperature crystallization method, a cooling crystallization method, a solvent-evaporation crystallization method or a crystal seed-induced crystallization method.

The present disclosure also relates to a method for preparing crystal form A of the compound of formula (I), which comprises: taking an amount of the compound of formula (I), adding an appropriate amount of ethyl acetate for dissolution, heating same until the solution is clear, adding n-hexane until a turbid solution appears, slowly cooling the solution to room temperature and stirring for crystallization to obtain crystal form A. The present disclosure also relates to a method for preparing crystal form A of the compound of formula (I), which comprises: taking an amount of the compound of formula (I), adding an appropriate amount of dichloromethane for dissolution, heating same until the solution is clear, adding an appropriate amount of isopropyl ether, slowly cooling the solution to room temperature and stirring for crystallization to obtain crystal form A. The present disclosure also relates to a method for preparing crystal form A of the compound of formula (I), which comprises: taking an amount of the compound of formula (I), adding an appropriate amount of acetone for dissolution, heating same until the solution is clear, adding an appropriate amount of n-heptane, slowly cooling the solution to room temperature and stirring for crystallization to obtain crystal form A. The present disclosure also relates to a method for preparing crystal form A of the compound of formula (I), which comprises: taking an amount of the compound of formula (I), adding an appropriate amount of ethyl acetate for dissolution, heating same until the solution is clear, adding an appropriate amount of n-heptane, slowly cooling the solution to room temperature and stirring for crystallization to obtain crystal form A. The present disclosure also relates to a method for preparing crystal form A of the compound of formula (I), which comprises: taking an amount of the compound of formula (I), adding an appropriate amount of toluene for dissolution, heating same until the solution is clear, adding an appropriate amount of n-heptane, slowly cooling the solution to room temperature and stirring for crystallization to obtain crystal form A. The present disclosure also relates to a method for preparing crystal form A of the compound of formula (I), which comprises: taking an amount of the compound of formula (I), adding an appropriate amount of ethyl formate for dissolution, heating same until the solution is clear, adding an appropriate amount of n-hexane with a small amount of solid being precipitated, slowly cooling the solution to room temperature and stirring for crystallization to obtain crystal form A. The present disclosure also relates to a method for preparing crystal form A of the compound of formula (I), which comprises: taking an amount of the compound of formula (I), adding an appropriate amount of ethyl acetate for dissolution, heating same until the solution is clear, adding an appropriate amount of n-hexane until solid is precipitated, further stirring the solution under a heating state for a period of time, slowly cooling the solution to room temperature and stirring for crystallization to obtain crystal form A.

The present disclosure also relates to a method for preparing crystal form A of the compound of formula (I), which comprises: taking an amount of crystal form B of the compound of formula (I), adding same to an appropriate amount of toluene and slurrying the mixture at room temperature to obtain crystal form A. The present disclosure also relates to a method for preparing crystal form A of the compound of formula (I), which comprises: taking an amount of crystal form B of the compound of formula (I), adding same to an appropriate amount of a mixed solvent of tetrahydrofuran/methyl tert-butyl ether and slurrying the mixture at room temperature to obtain crystal form A. The present disclosure also relates to a method for preparing crystal form A of the compound of formula (I), which comprises: taking an amount of crystal form B of the compound of formula (I), adding same to an appropriate amount of a mixed solvent of ethyl acetate/n-hexane and slurrying the mixture at room temperature to obtain crystal form A. The present disclosure also relates to a method for preparing crystal form A of the compound of formula (I), which comprises: taking an amount of crystal form B of the compound of formula (I), adding same to an appropriate amount of a mixed solvent of ethyl acetate/n-heptane and slurrying the mixture at room temperature to obtain crystal form A. The present disclosure also relates to a method for preparing crystal form A of the compound of formula (I), which comprises: taking an amount of crystal forms A and B of the compound of formula (I), adding same to an appropriate amount of a mixed solvent of dioxane/water and slurrying the mixture at room temperature to obtain crystal form A. The present disclosure also relates to a method for preparing crystal form A of the compound of formula (I), which comprises: taking an amount of crystal forms A and B of the compound of formula (I), adding same to an appropriate amount of acetonitrile and slurrying the mixture at room temperature to obtain crystal form A. The present disclosure also relates to a method for preparing crystal form A of the compound of formula (I), which comprises: taking an amount of crystal form A of the compound of formula (I), adding same to an appropriate amount of water and slurrying the mixture at room temperature to obtain crystal form A.

The present disclosure also relates to a method for preparing crystal form B of the compound of formula (I), which comprises: taking an amount of the compound of formula (I), adding an appropriate amount of ethyl acetate for dissolution, heating same until the solution is clear, adding n-heptane until a turbid solution appears, further stirring the solution under a heating state for a period of time, slowly cooling the temperature to 50° C. with solid being precipitated, further adding an appropriate amount of n-heptane, slowly cooling the temperature to 10° C., and stirring for crystallization to obtain crystal form B. The present disclosure also relates to a method for preparing crystal form B of the compound of formula (I), which comprises: taking an amount of the compound of formula (I), adding an appropriate amount of tetrahydrofuran, adding dropwise the solution to an isopropyl ether solution containing an amount of crystal seeds of crystal form A under room temperature, and stirring for crystallization to obtain crystal form B.

The present disclosure also relates to a method for preparing crystal form B of the compound of formula (I), which comprises: taking an amount of amorphous crystal forms of the compound of formula (I), adding same to an appropriate amount of a mixed solvent of tert-butyl acetate/methyl tert-butyl ether/n-hexane and slurrying the mixture at room temperature to obtain crystal form B. The present disclosure also relates to a method for preparing crystal form B of the compound of formula (I), which comprises: taking an amount of amorphous crystal forms of the compound of formula (I), adding same to an appropriate amount of a mixed solvent of trifluoroethanol/isopropyl ether and slurrying the mixture at elevated temperature to obtain crystal form B. The present disclosure also relates to a method for preparing crystal form B of the compound of formula (I), which comprises: taking an amount of amorphous crystal forms of the compound of formula (I), adding same to an appropriate amount of n-heptane and slurrying the mixture at elevated temperature to obtain crystal form B. The present disclosure also relates to a method for preparing crystal form B of the compound of formula (I), which comprises: taking an amount of an amorphous crystal form of the compound of formula (I), adding same to an appropriate amount of a mixed solvent of chloroform/methyl tert-butyl ether and slurrying the mixture at elevated temperature to obtain crystal form B. The present disclosure also relates to a method for preparing crystal form B of the compound of formula (I), which comprises: taking an amount of an amorphous crystal form of the compound of formula (I), adding an appropriate amount of methyl tert-butyl ether and slurrying the mixture at room temperature until same is insoluble at elevated temperature to obtain crystal form B. The present disclosure also relates to a method for preparing crystal form B of the compound of formula (I), which comprises: taking an amount of an amorphous crystal form of the compound of formula (I), adding an appropriate amount of cyclohexane and slurrying the mixture at room temperature until same is insoluble at elevated temperature to obtain crystal form B. The present disclosure also relates to a method for preparing crystal form B of the compound of formula (I), which comprises: taking an amount of crystal forms A and B of the compound of formula (I), adding same to an appropriate amount of the ethyl acetate/n-heptane mixed solvent and slurrying the mixture at room temperature to obtain crystal form B. The present disclosure also relates to a method for preparing crystal form B of the compound of formula (I), which comprises: taking an amount of crystal forms A and B of the compound of formula (I), adding same to an appropriate amount of the acetone/methyl tert-butyl ether/n-hexane mixed solvent and slurrying the mixture at room temperature to obtain crystal form B. The present disclosure also relates to a method for preparing crystal form B of the compound of formula (I), which comprises: taking an amount of crystal forms A and B of the compound of formula (I), adding same to an appropriate amount of the butyl acetate/methyl tert-butyl ether/n-hexane mixed solvent and slurrying the mixture at room temperature to obtain crystal form B.

The present disclosure also relates to a method for preparing crystal form C of the compound of formula (I), which comprises: taking an amount of the compound of formula (I), adding an appropriate amount of p-xylene and slurrying the mixture at room temperature for crystallization to obtain crystal form C.

The present disclosure also relates to a method for preparing crystal form D of the compound of formula (I), which comprises: taking an amount of the compound of formula (I), adding an appropriate amount of ethyl acetate for dissolution, heating same until the solution is clear, cooling the solution and stirring for crystallization to obtain crystal form D. The present disclosure also relates to a method for preparing crystal form D of the compound of formula (I), which comprises: taking an amount of the compound of formula (I), adding an appropriate amount of ethyl acetate for dissolution, heating same until the solution is clear, adding dropwise an appropriate amount of n-hexane, slowly cooling the solution and stirring for crystallization to obtain crystal form D. The present disclosure also relates to a method for preparing crystal form D of the compound of formula (I), which comprises: taking an amount of the compound of formula (I), adding an appropriate amount of acetone for dissolution, heating same until the solution is clear, adding dropwise an appropriate amount of n-heptane, slowly cooling the solution and stirring for crystallization to obtain crystal form D. The present disclosure also relates to a method for preparing crystal form D of the compound of formula (I), which comprises: taking an amount of the compound of formula (I), adding an appropriate amount of ethyl acetate for dissolution, adding dropwise an appropriate amount of n-hexane containing about 4 mg of crystal form A, and stirring for crystallization, to obtain crystal form D.

The present disclosure also relates to a method for preparing crystal form D of the compound of formula (I), which comprises: taking an amount of the compound of formula (I), adding an appropriate amount of acetone for dissolution, adding dropwise an appropriate amount of isopropyl ether containing about 4 mg of crystal form A, and stirring for crystallization, to obtain crystal form D. The present disclosure also relates to a method for preparing crystal form D of the compound of formula (I), which comprises: taking an amount of the compound of formula (I), adding an appropriate amount of the acetone/isopropyl ether mixed solvent and then slowly volatilizing at room temperature for crystallization to obtain crystal form D.

The present disclosure also relates to a method for preparing crystal form D of the compound of formula (I), which comprises: taking an amount of amorphous crystal forms of the compound of formula (I), adding same to an appropriate amount of acetonitrile and slurrying the mixture at room temperature to obtain crystal form D.

The present disclosure also relates to a method for preparing crystal form E of the compound of formula (I), which comprises: taking an amount of the compound of formula (I), adding an appropriate amount of the acetone/cyclohexane mixed solvent and then slowly volatilizing at room temperature for crystallization to obtain crystal form E.

The present disclosure also relates to a method for preparing crystal form F of the compound of formula (I), which comprises: taking an amount of the compound of formula (I), adding an appropriate amount of ethyl acetate, heating same until the solution is clear, further stirring the solution with solid being precipitated, adding dropwise an appropriate amount of n-hexane, slowly cooling the solution and stirring for crystallization to obtain crystal form F. The present disclosure also relates to a method for preparing crystal form F of the compound of formula (I), which comprises: taking an amount of the compound of formula (I), adding an appropriate amount of ethyl formate and heating to reflux until the solution is clear, adding dropwise an appropriate amount of n-hexane, adding crystal seeds of crystal form F and heating to reflux until the solution is clear, slowly cooling the solution and stirring for crystallization to obtain crystal form F.

The present disclosure also relates to a method for preparing crystal form F of the compound of formula (I), which comprises: taking an amount of amorphous crystal forms of the compound of formula (I), adding same to an appropriate amount of the 1,4-dioxane/water mixed solvent and slurrying the mixture at room temperature to obtain crystal form F. The present disclosure also relates to a method for preparing crystal form F of the compound of formula (I), which comprises: taking an amount of crystal form A of the compound of formula (I), adding same to an appropriate amount of the acetonitrile/water mixed solvent and slurrying the mixture at room temperature to obtain crystal form F. The present disclosure also relates to a method for preparing crystal form F of the compound of formula (I), which comprises: taking an amount of crystal form A of the compound of formula (I), adding same to an appropriate amount of the tetrahydrofuran/water mixed solvent and slurrying the mixture at room temperature to obtain crystal form F. The present disclosure also relates to a method for preparing crystal form F of the compound of formula (I), which comprises: taking an amount of crystal form A of the compound of formula (I), adding same to an appropriate amount of the acetone/water mixed solvent and slurrying the mixture at room temperature to obtain crystal form F. The present disclosure also relates to a method for preparing crystal form F of the compound of formula (I), which comprises: taking an amount of crystal form A of the compound of formula (I), adding same to an appropriate amount of the isopropanol/water mixed solvent and slurrying the mixture at room temperature to obtain crystal form F. The present disclosure also relates to a method for preparing crystal form F of the compound of formula (I), which comprises: taking an amount of amorphous crystal forms of the compound of formula (I), adding same to an appropriate amount of the ethyl propionate/n-heptane mixed solvent and slurrying the mixture at room temperature to obtain crystal form F.

The present disclosure also relates to a pharmaceutical composition comprising crystal form A, crystal form B, crystal form C, crystal form D, crystal form E or crystal form F of the compound of formula (I) and optionally one or more pharmaceutically acceptable carriers and/or diluents. The pharmaceutical composition can be prepared into any one of the pharmaceutically acceptable dosage forms. For example, the pharmaceutical formulation comprising crystal form A, crystal form B, crystal form C, crystal form D, crystal form E or crystal form F of the compound of formula (I) of the present disclosure can be prepared into a tablet, a capsule, a pill, a granule, a solution, a suspension, a syrup, an injection (including an injectable solution, sterile powders for injection and a concentrated solution for injection), a suppository, an inhalant or a spray.

In addition, the pharmaceutical composition of the present disclosure can also be administered to patients or subjects in need of such treatment by any suitable administration route, such as oral, parenteral, rectal, pulmonary or topical administration route. When used for oral administration, the pharmaceutical composition can be prepared into an oral formulation, for example, an oral solid formulation such as a tablet, a capsule, a pill and a granule; or an oral liquid formulation such as an oral solution, an oral suspension and a syrup. When prepared into an oral formulation, the pharmaceutical formulation may also comprise suitable fillers, binders, disintegrants, lubricants, etc. When used for parenteral administration, the pharmaceutical formulation can be prepared into an injection, including an injectable solution, sterile powders for injection, and a concentrated solution for injection. When prepared into an injection, the pharmaceutical composition can be produced using conventional methods in the existing pharmaceutical field. When the pharmaceutical formulation is prepared into an injection, additives may not be added, or suitable additives can be added according to the properties of the drug. When used for rectal administration, the pharmaceutical formulation can be prepared into a suppository, etc. When used for pulmonary administration, the pharmaceutical formulation can be prepared into an inhalant, a spray, etc. In certain embodiments, crystal form A, crystal form B, crystal form C, crystal form D, crystal form E or crystal form F of the compound of formula (I) of the present disclosure is present in the pharmaceutical composition or drug in a therapeutically and/or prophylactically effective dose. In certain embodiments, crystal form A, crystal form B, crystal form C, crystal form D, crystal form E or crystal form F of the compound of formula (I) of the present disclosure is present in the pharmaceutical composition or drug in unit dosage form.

The present disclosure further relates to a method for preparing the pharmaceutical composition, which comprises: mixing one or more of crystal forms selected from crystal form A, crystal form B, crystal form C, crystal form D, crystal form E or crystal form F of the compound of formula (I) of the present disclosure with at least one pharmaceutically acceptable carrier, diluent or excipient.

The present disclosure further relates to an use of crystal form A, crystal form B, crystal form C, crystal form D, crystal form E or crystal form F of the compound of formula (I) in the manufacture of a medicament for treating and/or preventing factor XIa-mediated diseases.

The present disclosure further relates to an use of crystal form A, crystal form B, crystal form C, crystal form D, crystal form E or crystal form F of the compound of formula (I) in the manufacture of a medicament for treating and/or preventing cardiovascular and cerebrovascular diseases, wherein the cardiovascular and cerebrovascular diseases are selected from thromboembolic diseases, preferably myocardial infarction, angina, reocclusion and restenosis after angioplasty or aortic coronary artery bypass, disseminated intravascular coagulation, stroke, transient ischemia attack, peripheral arterial occlusive diseases, pulmonary embolism or deep vein thrombosis.

DETAILED DESCRIPTION OF THE PRESENT INVENTION

In the description and claims of the present application, all scientific and technical terms used herein have the meanings commonly understood by a person skilled in the art unless specified otherwise. However, to better understand the present disclosure, definitions and explanations of some related terms are provided below. In addition, when the definitions and explanations of terms provided in the present application have different meanings from those commonly understood by those of skill in the art, the definitions and explanations of terms provided in the present application shall control.

The "ether solvent" described in the present disclosure refers to a chain compound or cyclic compound containing an ether bond —O— and having 1 to 10 carbon atoms, and the specific examples thereof include, but are not limited to: tetrahydrofuran, diethyl ether, propylene glycol methyl ether, methyl tert-butyl ether, isopropyl ether or 1,4-dioxane.

The "alcohol solvent" described in the present disclosure refers to a group derived from "C1-6 alkyl" on which one or more hydrogen atoms are substituted with one or more "hydroxyl groups", wherein the "hydroxyl group" and "C1-6 alkyl" are as defined above, and the specific examples thereof include, but are not limited to: methanol, ethanol, isopropanol, n-propanol, isopentanol or trifluoroethanol.

The "ester solvent" described in the present disclosure refers to a complex of a lower organic acid containing 1 to 4 carbon atoms and a lower alcohol containing 1 to 6 carbon atoms, and the specific examples thereof include, but are not limited to: ethyl acetate, ethyl formate, tert-butyl acetate, ethyl propionate, isopropyl acetate or butyl acetate.

The "ketone solvent" described in the present disclosure refers to a compound in which a carbonyl group (—C(O)—) is connected to two hydrocarbon groups. According to the difference of the hydrocarbon group in the molecule, ketones can be divided into aliphatic ketones, alicyclic ketones, aromatic ketones, saturated ketones and unsaturated ketones. Specific examples of ketone solvents include, but are not limited to: acetone, acetophenone, 4-methyl-2-pentanone, 2-butanone and methyl isobutyl ketone.

The "nitrile solvent" described in the present disclosure refers to a group derived from "C1-6 alkyl" on which one or more hydrogen atoms are substituted with one or more "cyano groups", wherein the "cyano group" and "C1-6 alkyl" are as defined above, and the specific examples thereof include, but are not limited to: acetonitrile or propionitrile.

The "halogenated hydrocarbon solvent" described in the present disclosure refers to a group derived from "C1-6 alkyl" on which one or more hydrogen atoms are substituted with one or more "halogen groups", wherein the "halogen group" and "C1-6 alkyl" are as defined above, and the specific examples thereof include, but are not limited to: chloromethane, dichloromethane, 1,2-dichloroethane, chloroform or tetrachloromethane.

The "X-ray powder diffraction pattern or XRPD" described in the present disclosure is obtained by using Cu—Kα ray diffraction.

The "differential scanning calorimetry or DSC" described in the present disclosure is used to obtain phase change information of samples by measuring the temperature difference and heat flow difference between the samples and reference materials during heating process or constant temperature process and then characterizing all physical and chemistry changes related to thermal effects.

The "2θ or 2θ angle" described in the present disclosure refers to the diffraction angle, wherein θ is the Bragg angle in the unit of ° or degree, and the error range of the 2θ is ±0.1 to ±0.5, preferably ±0.1 to ±0.3, more preferably ±0.2.

Beneficial Effects of the Invention

Crystal form A, crystal form B, crystal form C, crystal form D, crystal form E and crystal form F of (S)-4-(4-(tert-butoxy)-2-(4-(5-chloro-2-propionylphenyl)-5-methoxy-2-oxopyridin-1(2H)-yl)butanamido)benzoic acid (the compound of formula (I)) provided in the present disclosure have more advantages in solubility, stability, and hygroscopicity and are thus more suitable for drug development. Said crystal forms meet requirements of bioavailability and efficacy and medicinal requirements in production, transportation and storage, leading to a stable, repeatable and controllable production process which can be adapted to industrial production.

DETAILED DESCRIPTION OF THE PREFERRED EMBODIMENTS

Figure 1:
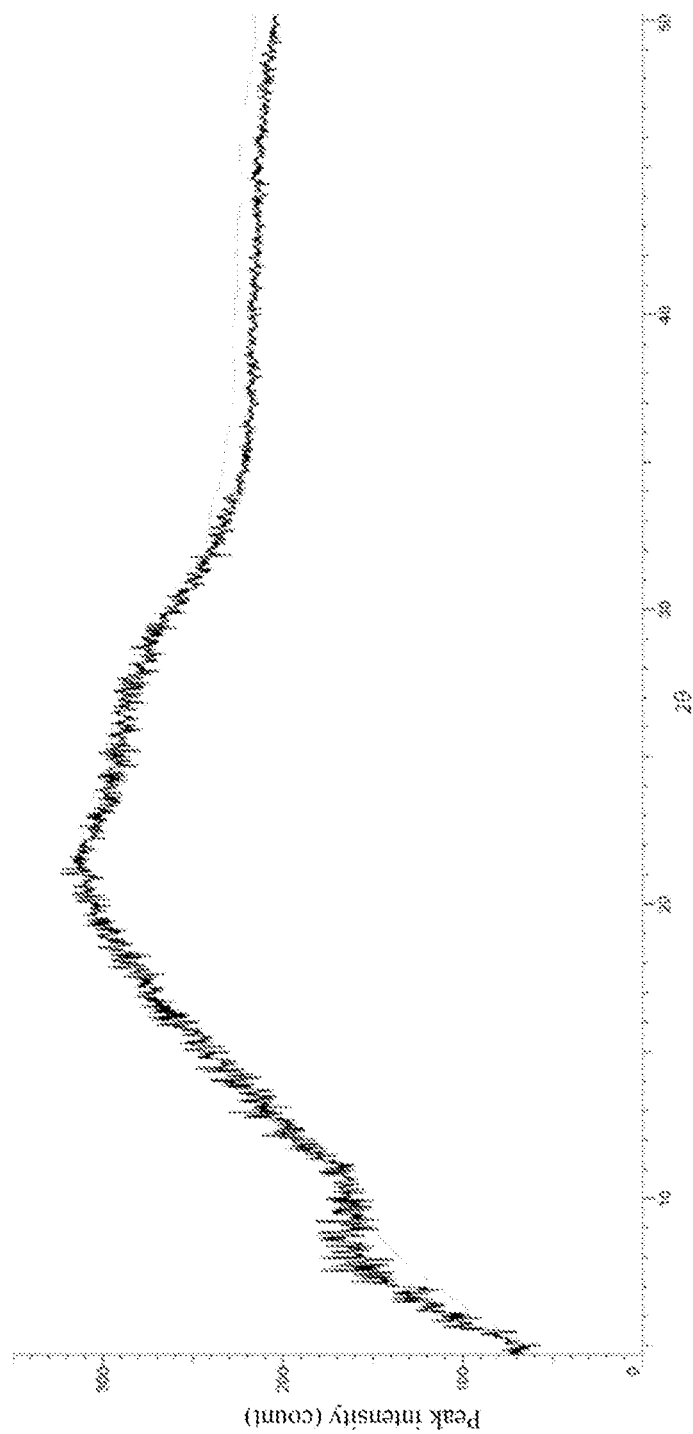
FIG. 1 is the XRPD pattern of the compound of formula (I) present in an amorphous form.

The present disclosure will be explained in more detail in combination with examples as below, and the examples of the present disclosure are merely used for describing the technical solution of the present disclosure but for limiting the essence and scope of the present disclosure.

Test conditions for instruments used in the experiment:

the structures of the compounds are determined by nuclear magnetic resonance (NMR) and/or mass spectrometry (MS). NMR shift (δ) is given in the unit of $10^{-6}$ (ppm). NMR is determined by Bruker AVANCE-400 Nuclear Magnetic Resonance Spectrometer; the solvent for determination is deuterated dimethyl sulfoxide (DMSO-$d_6$), deuterated chloroform (CDCl$_3$), deuterated methanol (CD$_3$OD); and the internal standard is tetramethylsilane (TMS).

MS is determined by FINNIGAN LCQAd (ESI) mass spectrometer (manufacturer: Thermo, model: Finnigan LCQ advantage MAX).

HPLC is determined by Agilent 1200DAD High pressure Liquid Chromatograph (chromatographic column: Sunfire C18 150×4.6 mm) and Waters 2695-2996 High Pressure Liquid chromatograph (chromatographic column: Gimini C18 150×4.6 mm).

XRPD refers to X-ray powder diffraction and is determined using BRUKER D8 X-ray Diffractometer, with specific collecting information as follows: Cu anode (40 kV, 40 mA), Cu—Kα1 rays (λ=1.54060 Å), Kα2 rays (λ=1.54439 Å), and Kβ rays (λ=1.39222 Å); scanning range (2q range): 3° to 64°, scanning step length: 0.02, and slit width (collimator): 1.0 mm. A step-by-step scanning method is used, with the number of scanning steps of 3 steps, the scanning range of 19° per step, the starting degree of 10°, the ending degree of 48°, and the duration of 45 s per step.

DSC refers to differential scanning calorimetry and is determined using METTLER TOLEDO DSC 3+ Differential Scanning Calorimeter, with the heating rate of 10° C./min, wherein the specific temperature range is determined with reference to the corresponding diagram (mostly 25° C. to 300° C. or 25° C. to 350° C.), and the nitrogen purge rate of 50 mL/min.

TGA refers to thermogravimetric analysis and is determined using METTLER TOLEDO TGA 2 Thermogravimetric Analyzer, with the heating rate of 10° C./min, wherein the specific temperature range is determined with reference to the corresponding diagram (mostly 25° C. to 300° C. or 25° C. to 350° C.), and the nitrogen purge rate of 20 mL/min.

DVS refers to dynamic vapor sorption and is determined using SMS DVS Advantage at 25° C., with the humidity change of 50%-95%-0%-95%-50% and the stepping of 10% (5% for the last step) (the specific humidity range is determined in accordance with the corresponding plot, and the methods listed herein are those most commonly used), and the standard for determination is as follow: dm/dt is not more than 0.02%, and Tmax is not more than 360 min.

Unless otherwise indicated, the solution in the examples refers to an aqueous solution.

Unless otherwise indicated, the reaction temperature in the examples refers to room temperature, which is 20° C. to 30° C.

The progress of the reaction in the examples is monitored by means of thin layer chromatography (TLC). The developing solvent used in the reaction, the eluent system of column chromatography used in the purification of compounds and the developing solvent system of thin layer chromatography include: A: Dichloromethane/methanol system, B: n-hexane/ethyl acetate system, wherein the volume ratio of the solvent is adjusted according to the polarity of compounds and can also be adjusted by adding a small quantity of basic reagents such as triethylamine or acidic reagents such as acetic acid.

Preparation Examples of the Compound of Formula (I) (The Preparation Method of Example 108 in WO 2018041122 A)

(S)-4-(4-(tert-butoxy)-2-(4-(5-chloro-2-propionylphenyl)-5-methoxy-2-oxopyridin-1(2H)-yl)butanamido)benzoic Acid 1

1 Compound of formula (I)

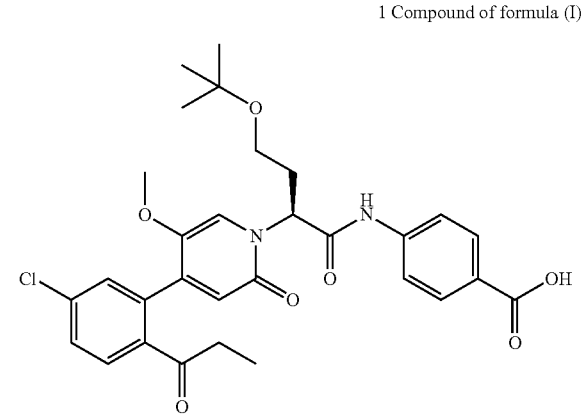 [SMILES: CCC(=O)c1ccc(Cl)cc1-c1cc(=O)n([C@@H](CCOC(C)(C)C)C(=O)Nc2ccc(C(=O)O)cc2)cc1OC]

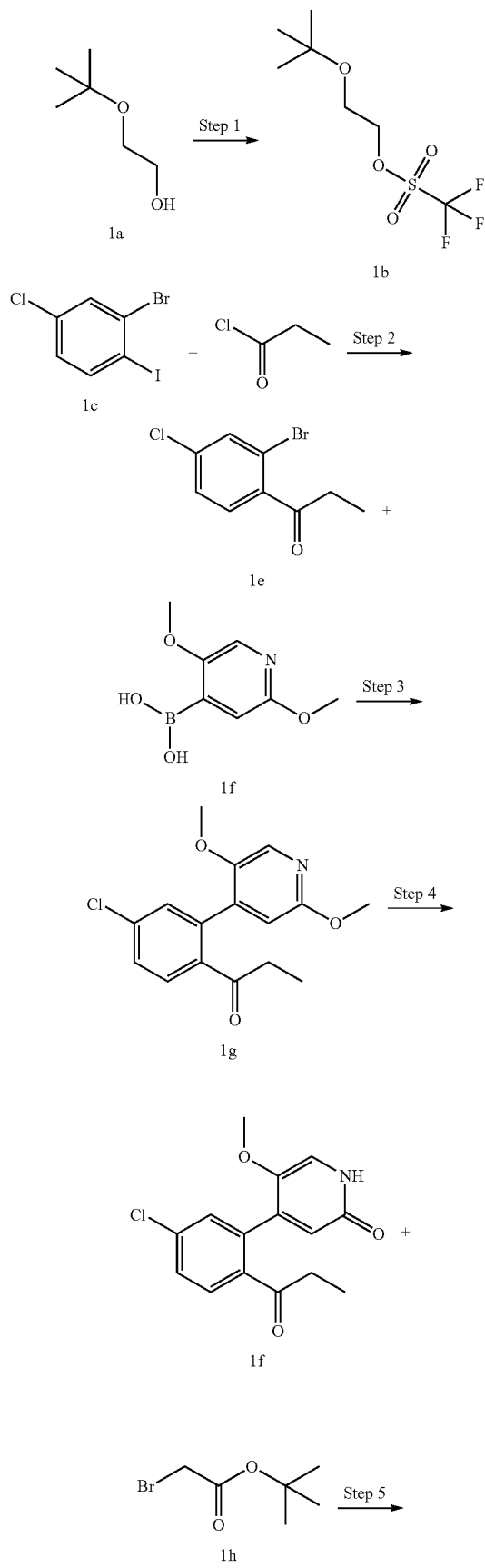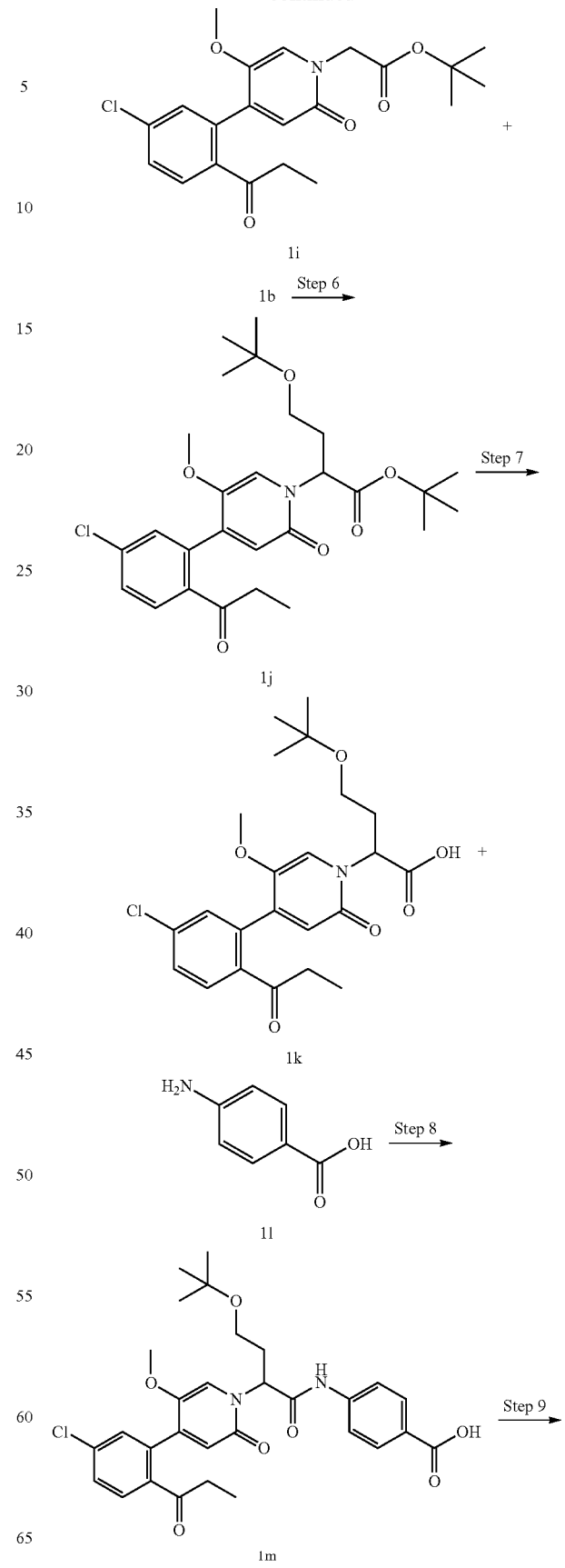

17

-continued

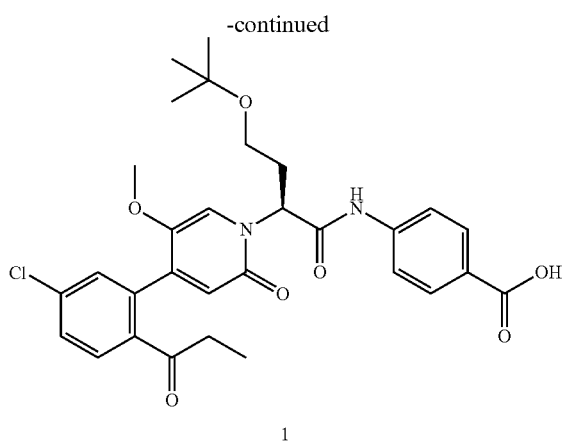

1

First Step 2-(Tert-butoxy)ethyl trifluoromethanesulfonate 1b

2-Tert-butoxy ethanol 1a (300 mg, 2.54 mmol) is dissolved in 8 mL of dichloromethane, added with 2,6-dimethylpyridine (299.22 mg, 2.79 mmol) in an ice bath, and added dropwise with trifluoromethanesulfonic anhydride (787.87 mg, 2.79 mmol); after completion of the dropwise addition, the reaction was stirred for 1 hour in an ice bath, allowed to naturally warm to room temperature and then stirred for 1 hour. The reaction solution was added with 30 mL of dichloromethane and washed with 20 mL of water; the organic phase was dried over anhydrous sodium sulfate, filtered, and concentrated under reduced pressure to obtain crude title compound 1b (550 mg); the product was used directly for the next reaction without purification.

Second Step 1-(2-Bromo-4-chlorphenyl)propane-1-one 1e

2-Bromo-4-chloro-1-iodobenzene 1c (1.0 g, 3.15 mmol, prepared by a well-known method in "*Angewandte Chemie, International Edition,* 2010, 49(46), 8729-8732") was dissolved in 1 mL of tetrahydrofuran, cooled to −20° C., added with isopropyl magnesium chloride (421.15 mg, 4.10 mmol), and reacted for 1 hour in advance. Propionyl chloride 1d (378.89 mg, 4.10 mmol), lithium chloride (11.42 mg, 189.00 µmol), cuprous chloride (9.36 mg, 94.50 µmol) and aluminum trichloride (12.61 mg, 94.50 µmol) were added to 1 mL of tetrahydrofuran and stirred uniformly at room temperature; to the mixed solution, the reaction solution that was reacted for 1 hour in advance was added dropwise, and the mixture was reacted at room temperature for 2 hours. To the reaction solution, 20 mL of saturated ammonium chloride solution was added to quench the reaction and extracted with dichloromethane (20 mL×3); the organic phases were combined, dried over anhydrous sodium sulfate and filtered, and the filtrate was concentrated under reduced pressure; the resulting residue was purified using CombiFlash (flash preparative instrument) with eluent B to obtain title compound 1e (640 mg, yield: 82.0%)

Third Step 1-(4-Chloro-2-(2,5-dimethoxypyridine-4-yl)phenyl)propane-1-one 1g

Compound 1e (640 mg, 2.59 mmol), compound 1f (520.41 mg, 2.84 mmol, prepared by the method disclosed in the patent application "WO 2015063093"), [1,1'-bis(diphenylphosphino)ferrocene]palladium dichloride (191.8 mg, 0.259 mmol) and sodium carbonate (822.16 mg, 7.76 mmol) were added to a mixed solvent of 20 mL of 1,4-dioxane and 4 mL of water, and after the addition, the reaction solution was heated to 85° C., and the reaction was stirred for 16 hours. The reaction solution was naturally cooled to room temperature, added with 20 mL of water and extracted with ethyl acetate (20 mL×3); the organic phases were combined, washed with water (30 mL) and saturated sodium chloride solution (30 mL), respectively, dried over anhydrous sodium sulfate and filtered, and the filtrate was concentrated under reduced pressure; the resulting residue was purified by silica gel column chromatography with eluent system B to obtain title compound 1g (600 mg, yield: 75.9%).

MS m/z (ESI): 306.0 [M+1]

Fourth Step 4-(5-Chloro-2-propionylphenyl)-5-methoxypyridine-2(1H)-one 1f

Compound 1g (600 mg, 1.96 mmol) was added to 10 mL of N,N-dimethylformamide, and pyridine hydrobromide (1.51 g, 9.81 mmol) was added; after the addition, the reaction was heated to 100° C. and stirred for 3 hours. The reaction solution was cooled to room temperature and concentrated under reduced pressure to remove the organic solvent; the resulting residue was added with 30 mL of water and extracted with dichloromethane (20 mL×3); the organic phases were combined, dried over anhydrous sodium sulfate and filtered, and the filtrate was concentrated under reduced pressure to obtain crude title compound 1f (550 mg). The product was used directly for the next reaction without purification.

MS m/z (ESI): 292.0 [M+1]

Fifth Step

Tert-butyl 2-(4-(5-chloro-2-propionylphenyl)-5-methoxy-2-oxypyridine-1(2H)-yl)acetate 1i Crude compound 1f (550 mg, 1.89 mmol), cesium carbonate (1.84 g, 5.67 mmol) and compound 1h (551.61 mg, 2.83 mmol, synthesized and obtained by a well-known method in "*Chemical Communications (Cambridge, United Kingdom),* 2012, 48(22), 2803-2805") were dissolved in 10 mL of N,N-dimethylformamide; after the addition, the reaction solution was heated to 65° C., and the reaction was stirred for 2 hours. The reaction solution was cooled to room temperature, added with 30 mL of water and extracted with ethyl acetate (30 mL×3); the organic phases were combined, washed with saturated sodium chloride solution (30 mL×3), dried over anhydrous sodium sulfate and filtered; the filtrate was concentrated under reduced pressure, and the resulting residue was purified by CombiFlash (flash preparative instrument) with eluent B to obtain title compound 1i (350 mg, yield: 51.0%).

MS m/z (ESI): 405.4 [M+1]

Sixth Step

Tert-butyl 4-(tert-butoxy)-2-(4-(5-chloro-2-propionylphenyl)-5-methoxy-2-oxypyridine-1(2H)-yl)butyrate 1j Compound 1i (148 mg, 364.65 µmol) and crude compound 1b (182.50 mg, 729.30 µmol) were dissolved in 15 mL of tetrahydrofuran; the reaction solution was cooled to −78° C. and added dropwise with bis(trimethylsilyl) lithium amide solution (1.46 mL, 1.46 mmol), and the reaction was stirred for 2 hours. At −78° C., the reaction solution was added slowly with 5 mL of water to quench the reaction. The reaction solution was allowed to naturally warm to room temperature, added with 20 mL of water and extracted with ethyl acetate (35 mL×3); the organic phases were combined, washed with saturated sodium chloride solution (25 mL×2), dried over anhydrous sodium sulfate and filtered, and the filtrate was concentrated under reduced pressure; the resulting residue was purified by silica gel column chromatography with eluent system A to obtain title compound 1j (120 mg, yield: 65.0%).

MS m/z (ESI): 506.5 [M+1]

Seventh Step 4-(tert-Butoxy)-2-(4-(5-chloro-2-propionylphenyl)-5-methoxy-2-oxypyridine-1(2H)-yl)butyric Acid 1k Compound 1j (120 mg, 237.14 μmol) was dissolved in a mixed solvent of 8 mL of ethanol and 4 mL of tetrahydrofuran; the reaction was added with lithium hydroxide (49.75 mg, 1.19 mmol), warmed to 50° C. and stirred for 2 hours. The reaction solution was cooled to room temperature, concentrated under reduced pressure to remove most of the organic solvent, added with 15 mL of water, adjusted to pH 3 with 3 M hydrochloric acid and extracted with ethyl acetate (20 mL×3); the organic phases were combined, washed with saturated sodium chloride solution (20 mL×2), dried over anhydrous sodium sulfate and filtered; and the filtrate was concentrated to obtain crude title compound 1k (106 mg). The product was used directly for the next reaction without purification.

MS m/z (ESI): 450.4 [M+1]

Eighth Step 4-(4-(Tert-butoxy)-2-(4-(5-chloro-2-propionylphenyl)-5-methoxy-2-oxypyridine-1(2H)-yl)butyrylamino)benzoic Acid 1m Crude compound 1k (106 mg, 235.59 μmol) was dissolved in 15 mL of ethyl acetate, and added successively with N,N-diisopropylethylamine (304.48 mg, 2.36 mmol), compound 1l (35.54 mg, 259.16 μmol, prepared and obtained by a well-known method in "*Angewandte Chemie—International Edition*, 2012, 51(34), 8564-8567") and 2,4,6-tripropyl-1,3,5,2,4,6-trioxatriphosphorinane-2,4,6-trioxide in ethyl acetate (50%, 599.70 mg, 942.38 μmol); after the addition, the reaction was warmed to 80° C. and stirred for 2 hours. The reaction solution was cooled to room temperature, added with 20 mL of water, adjusted to pH 5 with 3 M hydrochloric acid and extracted with ethyl acetate (20 mL×3); the organic phases were combined and washed with saturated sodium chloride solution (20 mL×2), dried over anhydrous sodium sulfate and filtered, and the filtrate was concentrated under reduced pressure; and the resulting residue was purified by high-performance liquid preparative instrument (Waters 2767-SQ detecor2; elution system: acetonitrile, water) to obtain title compound 1m (60 mg, yield: 44.8%).

MS m/z (ESI): 569.5 [M+1]

Ninth Step (S)-4-(4-(Tert-butoxy)-2-(4-(5-chloro-2-propionylphenyl)-5-methoxy-2-oxopyridin-1(2H)-yl)butanamido)benzoic Acid 1

Compound 1m (60 mg, 105.44 μmol) was subject to chiral preparative separation (separation conditions comprises chromatographic column: Superchiral S-AD (Chiralway), 2 cm I.D.*25 cm Length, 5 um; mobile phase: carbon dioxide: ethanol:diethylamine=60:40:0.05; flow rate: 50 g/min); and the corresponding components were collected and concentrated under reduced pressure to obtain title compound 1 (22 mg).

Detected by X-ray powder diffraction, the product was present in an amorphous form, as shown in FIG. 1.

Example 1. Preparation of Crystal Form A

The compound of formula (I) (3.3 g) was added to 10 mL of ethyl acetate, and the reaction solution was warmed to 80° C., stirred until the solution was clear, slowly added with n-hexane (about 15 mL) until a turbid solution appears, slowly cooled to room temperature with white solid being precipitated, and stirred at room temperature for another 3 hours. The reaction solution was filtered, and the filter cake was collected and dried in vacuum to obtain the product (2 g).

Figure 2:
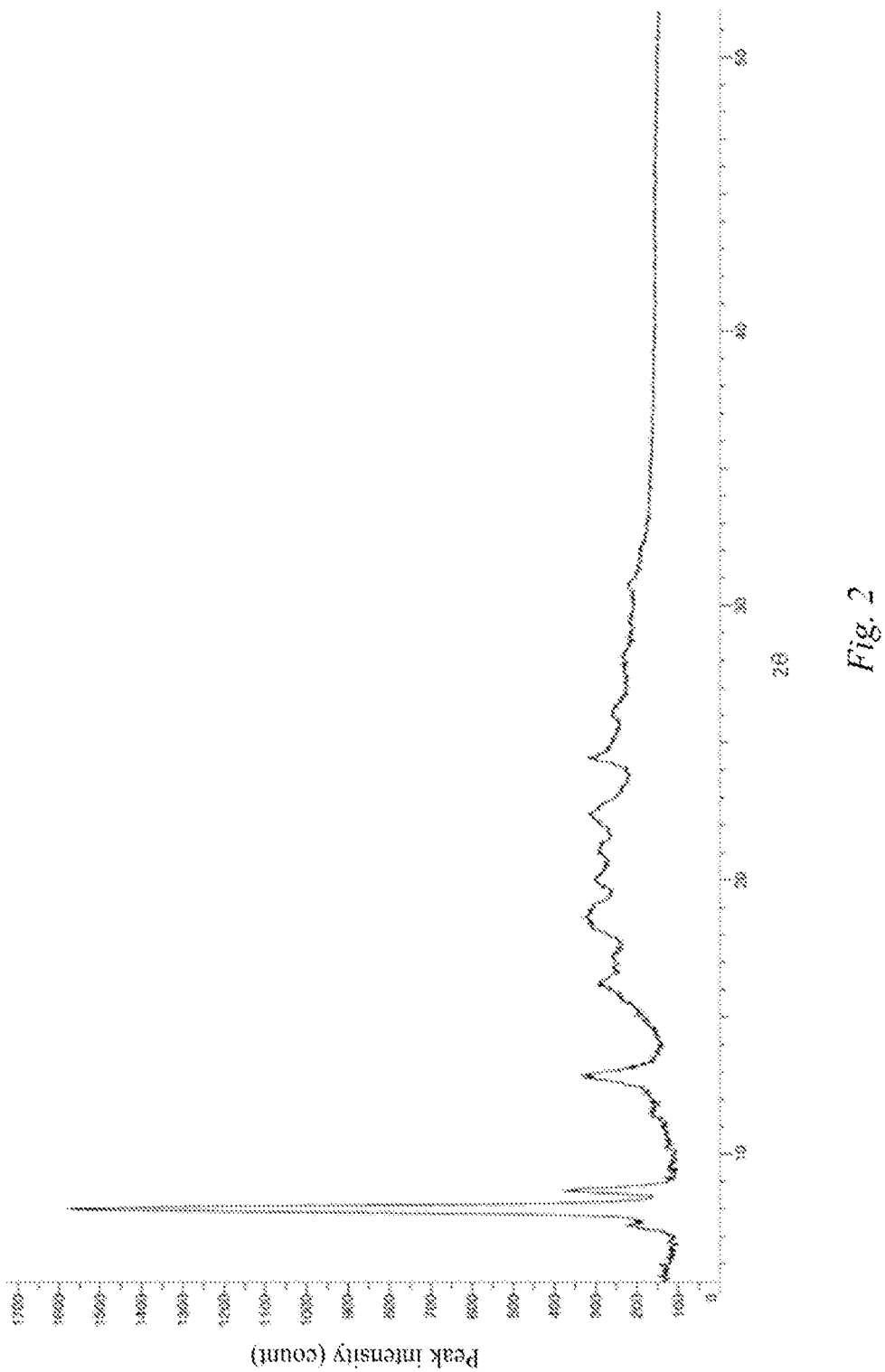
FIG. 2 is the XRPD pattern of the compound of formula (I) present in crystal form A.

Detected by X-ray powder diffraction, the product was defined as crystal form A. The XRPD spectrum is as shown in FIG. 2.

Figure 3:
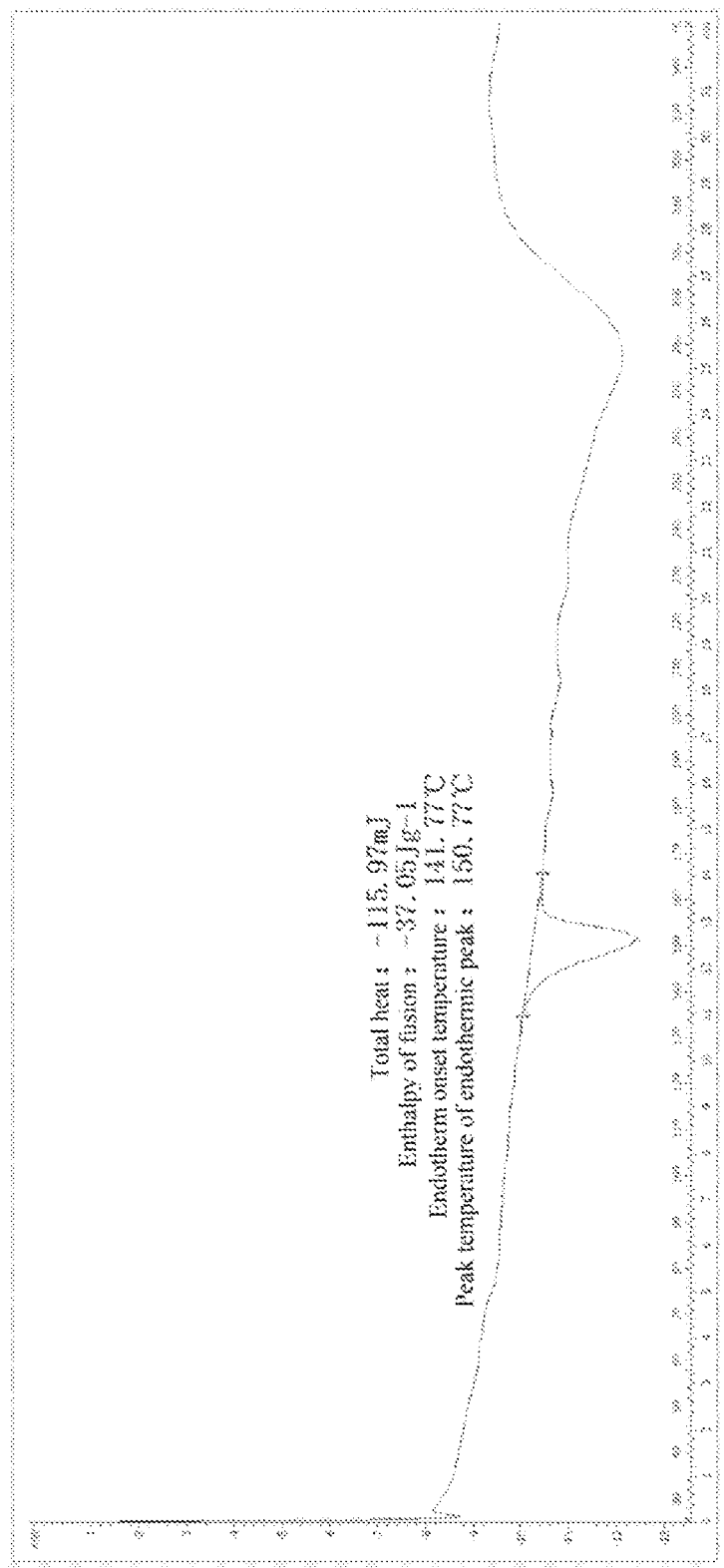
FIG. 3 is the DSC diagram of the compound of formula (I) present in crystal form A.
Figure 4:
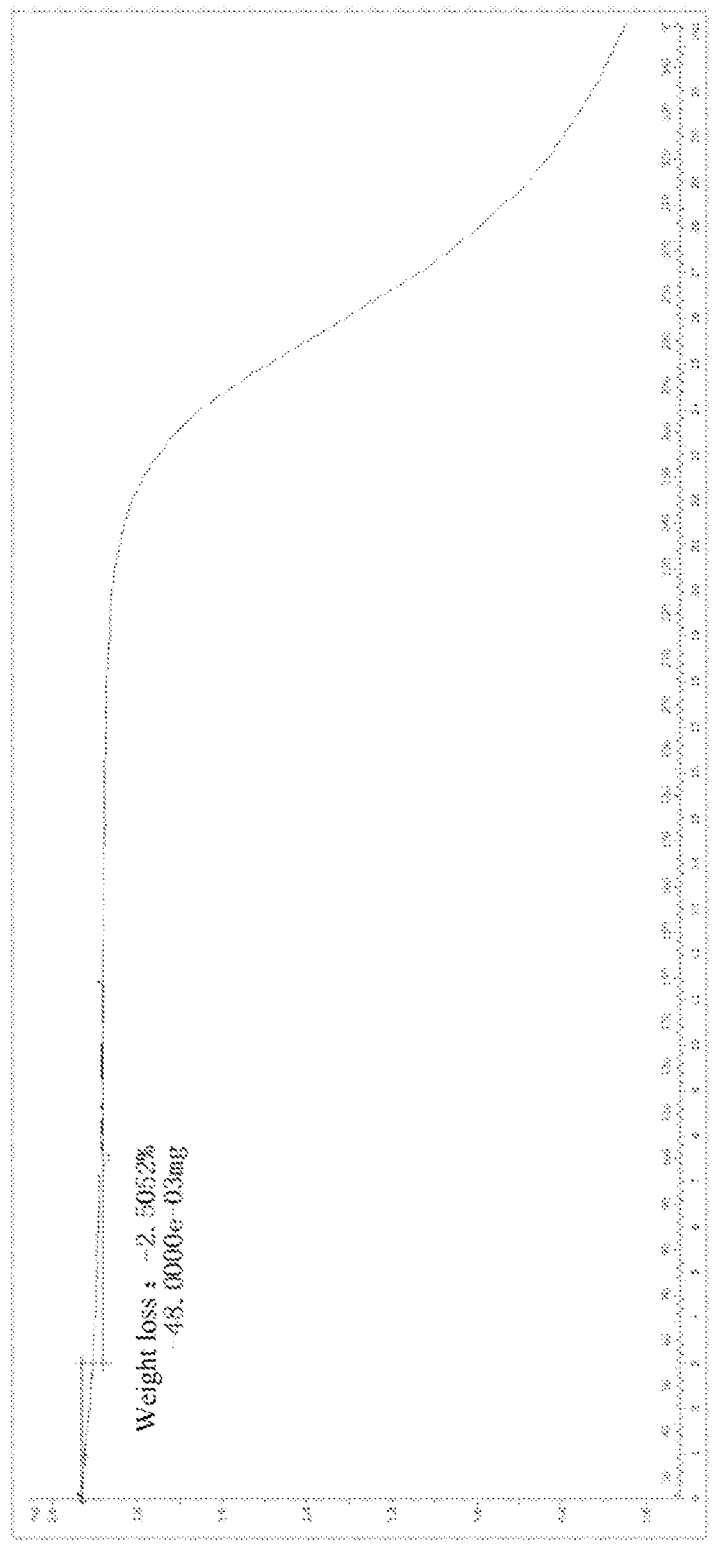
FIG. 4 is the TGA diagram of the compound of formula (I) present in crystal form A.

The DSC spectrum is as shown in FIG. 3, with the peak temperature of the endothermic peak of 150.77° C. The TGA spectrum is as shown in FIG. 4, with weight loss of 2.51% at 25° C. to 140° C.

Figure 5:
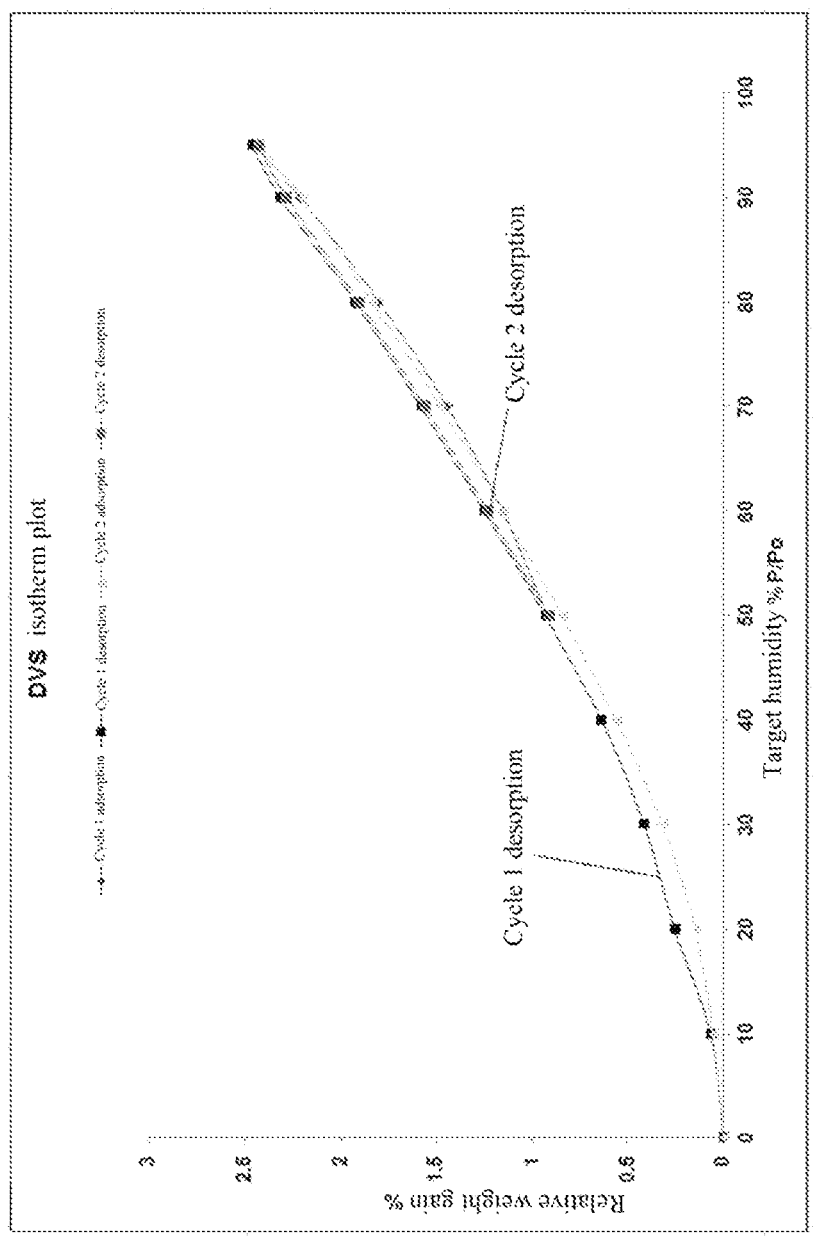
FIG. 5 is the DVS plot showing the hygroscopicity of the compound of formula (I) present in crystal form A.
Figure 6:
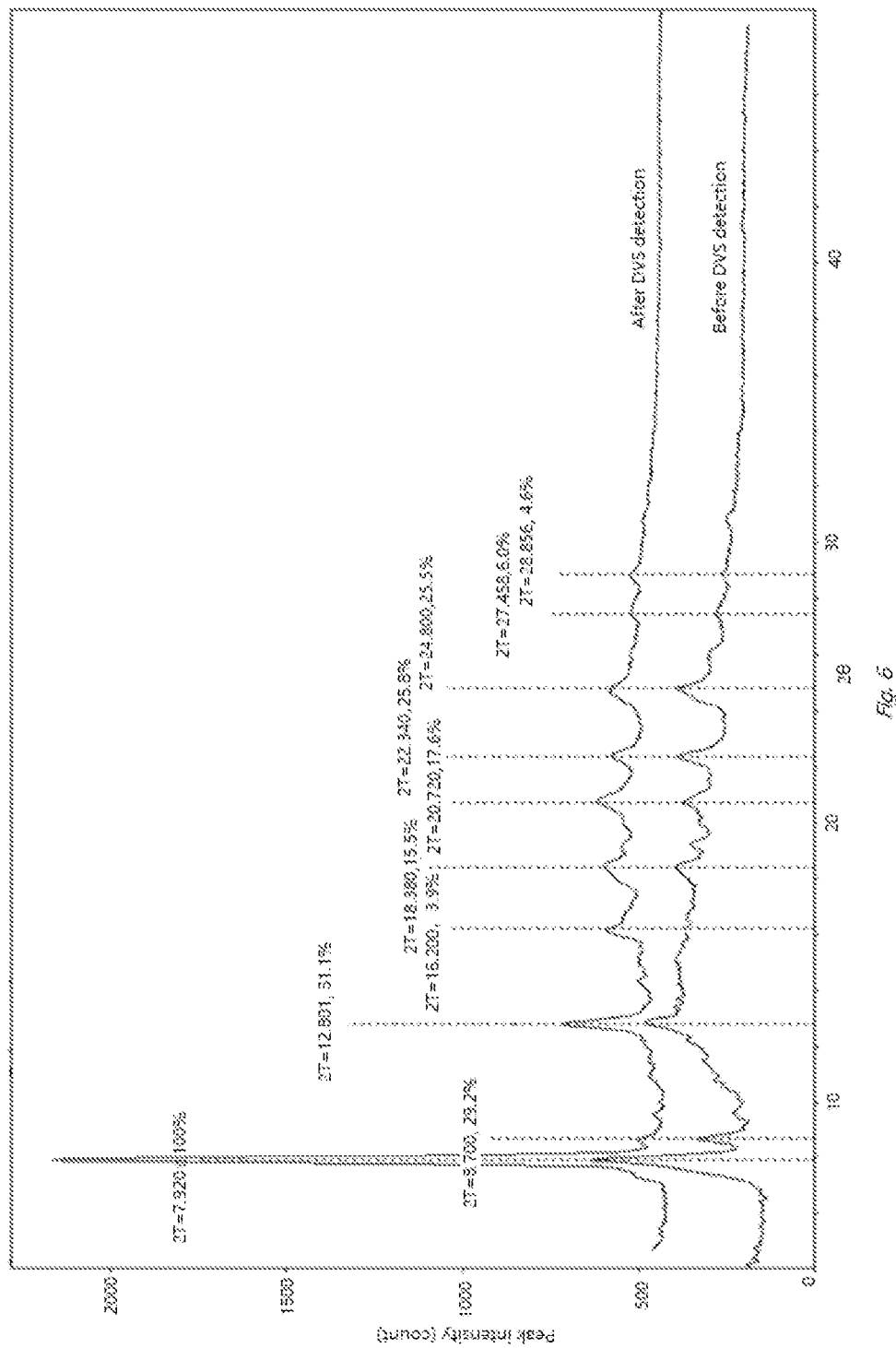
FIG. 6 is the XRPD pattern comparing the compound of formula (I) present in crystal form A before DVS detection and after DVS detection.

DVS characterization: According to the relative mass change curve, when the sample was stored at 25° C. and in the range of 10% RH to 80% RH, as the humidity increases, the mass was increased by about 1.781%, which was less than 2% but not less than 0.2%; and according to guidelines for drug hygroscopicity test in China Pharmacopoeia (2015 edition), the sample is slightly hygroscopic. When the sample was stored under normal conditions (i.e., 25° C. and 60% RH), the mass was increased by about 1.156%; when the sample was stored under accelerated test conditions (i.e., 70% RH), the mass was increased by about 1.479%; and when the sample was stored under extreme conditions (i.e., 90% RH), the mass was increased by about 2.199%. During a humidity change from 0% to 95%, the desorption process and adsorption process of the sample basically coincide. The DVS detection spectrum is as shown in FIG. 5, and the comparison for X-ray powder diffraction before and after DVS detection is as shown in FIG. 6, which indicates that the crystal form is unchanged before and after DVS detection.

TABLE 1

Characteristic peaks of crystal form A

| Peak number | 2-Theta | d(A) | I% |
|---|---|---|---|
| Peak 1 | 7.420 | 11.905 | 6.0 |
| Peak 2 | 8.000 | 11.043 | 100.0 |
| Peak 3 | 8.642 | 10.224 | 14.8 |
| Peak 4 | 12.900 | 6.857 | 12.6 |
| Peak 5 | 16.281 | 5.440 | 4.0 |
| Peak 6 | 18.280 | 4.849 | 3.8 |

TABLE 1-continued

Characteristic peaks of crystal form A

| Peak number | 2-Theta | d(A) | I% |
|---|---|---|---|
| Peak 7 | 20.018 | 4.432 | 2.9 |
| Peak 8 | 21.119 | 4.203 | 1.7 |
| Peak 9 | 22.400 | 3.966 | 4.6 |
| Peak 10 | 24.458 | 3.636 | 6.2 |
| Peak 11 | 26.100 | 3.411 | 1.6 |

Example 2. Preparation of Crystal Form A

The compound of formula (I) (100 mg) was added to 1 mL of dichloromethane, warmed to 50° C., stirred until the solution was clear, slowly added dropwise with 0.8 mL of isopropyl ether, slowly cooled to room temperature, and stirred for another 17 hours. The reaction solution was filtered, and the filter cake was collected and dried in vacuum to obtain the product (82 mg). Detected by X-ray powder diffraction, the product was present in crystal form A.

Example 3. Preparation of Crystal Form A

The compound of formula (I) (100 mg) was added to 1 mL of acetone, warmed to 50° C., stirred until the solution was clear, slowly added dropwise with 1.4 mL of n-heptane, slowly cooled to room temperature, and stirred for another 17 hours. The reaction solution was filtered, and the filter cake was collected and dried in vacuum to obtain the product (75 mg). Detected by X-ray powder diffraction, the product was present in crystal form A.

Example 4. Preparation of Crystal Form A

The compound of formula (I) (100 mg) was added to 0.8 mL of ethyl acetate, warmed to 80° C., stirred until the solution was clear, slowly added dropwise with 0.7 mL of n-heptane, slowly cooled to room temperature, and stirred for another 17 hours. The reaction solution was filtered, and the filter cake was collected and dried in vacuum to obtain the product (74 mg). Detected by X-ray powder diffraction, the product was present in crystal form A.

Example 5. Preparation of Crystal Form A

The compound of formula (I) (100 mg) was added to 1 mL of toluene, warmed to 110° C., stirred until the solution was clear, slowly added dropwise with 0.25 mL of n-heptane, slowly cooled to room temperature, and stirred for another 17 hours. The reaction solution was filtered, and the filter cake was collected and dried in vacuum to obtain the product (41 mg). Detected by X-ray powder diffraction, the product was present in crystal form A.

Example 6. Preparation of Crystal Form A

The compound of formula (I) (200 mg) was added to 4 mL of ethyl formate, warmed to 60° C., stirred until the solution was clear, slowly added dropwise with 5 mL of n-hexane, stirred for 15 minutes with a small amount of solid being precipitated, slowly cooled to 20° C. (about 3 hours) and stirred for another 13 hours. The reaction solution was filtered, and the filter cake was collected and dried in vacuum to obtain the product (100 mg). Detected by X-ray powder diffraction, the product was present in crystal form A.

Example 7. Preparation of Crystal Form A

The compound of formula (I) (200 mg) was added to 1 mL of ethyl acetate, warmed to 80° C., stirred until the solution was clear, slowly added dropwise with 1.5 mL of n-hexane with solid being precipitated, stirred for another 3 hours at 80° C., slowly cooled to 15° C. (about 3 hours) and stirred for another 14 hours. The reaction solution was filtered, and the filter cake was collected and dried in vacuum to obtain the product (130 mg). Detected by X-ray powder diffraction, the product was present in crystal form A.

Example 8. Preparation of Crystal Form B

Figure 7:
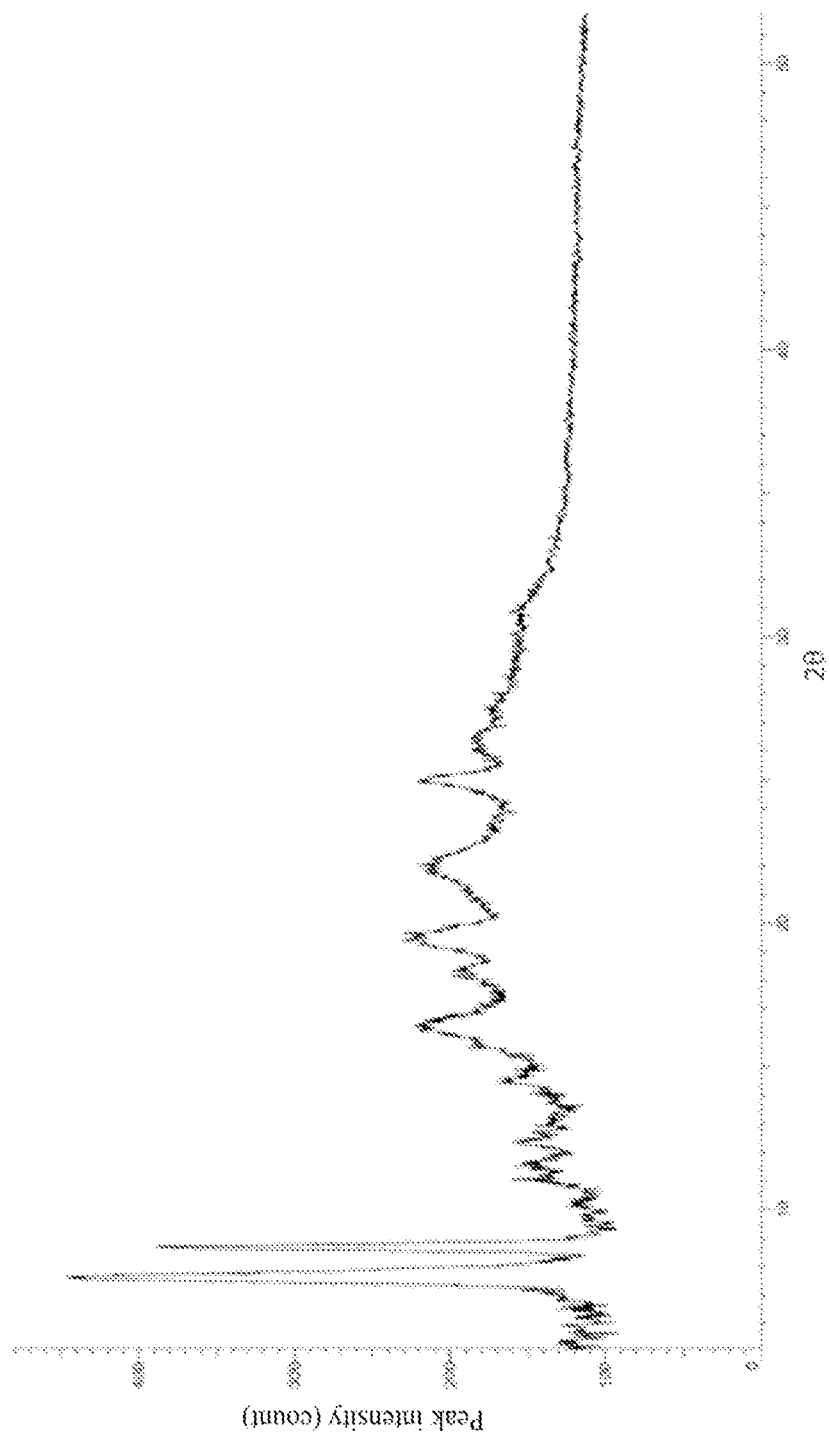
FIG. 7 is the XRPD pattern of the compound of formula (I) present in crystal form B.

The compound of formula (I) (4 g) was added to 8 mL of ethyl acetate, warmed to 80° C., stirred until the solution was clear, slowly added dropwise with 6 mL of n-heptane with a small amount of substance being precipitated and a turbid solution appearing, stirred for another 10 minutes at 80° C., slowly cooled to 50° C. with solid being precipitated, slowly added dropwise with another 6 mL of n-heptane, slowly cooled to 10° C. and stirred for another 17 hours. The reaction solution was filtered, and the filter cake was collected and dried in vacuum to obtain the product (3.5 g). Detected by X-ray powder diffraction, the product was defined as crystal form B. The spectrum is as shown in FIG. 7.

Figure 8:
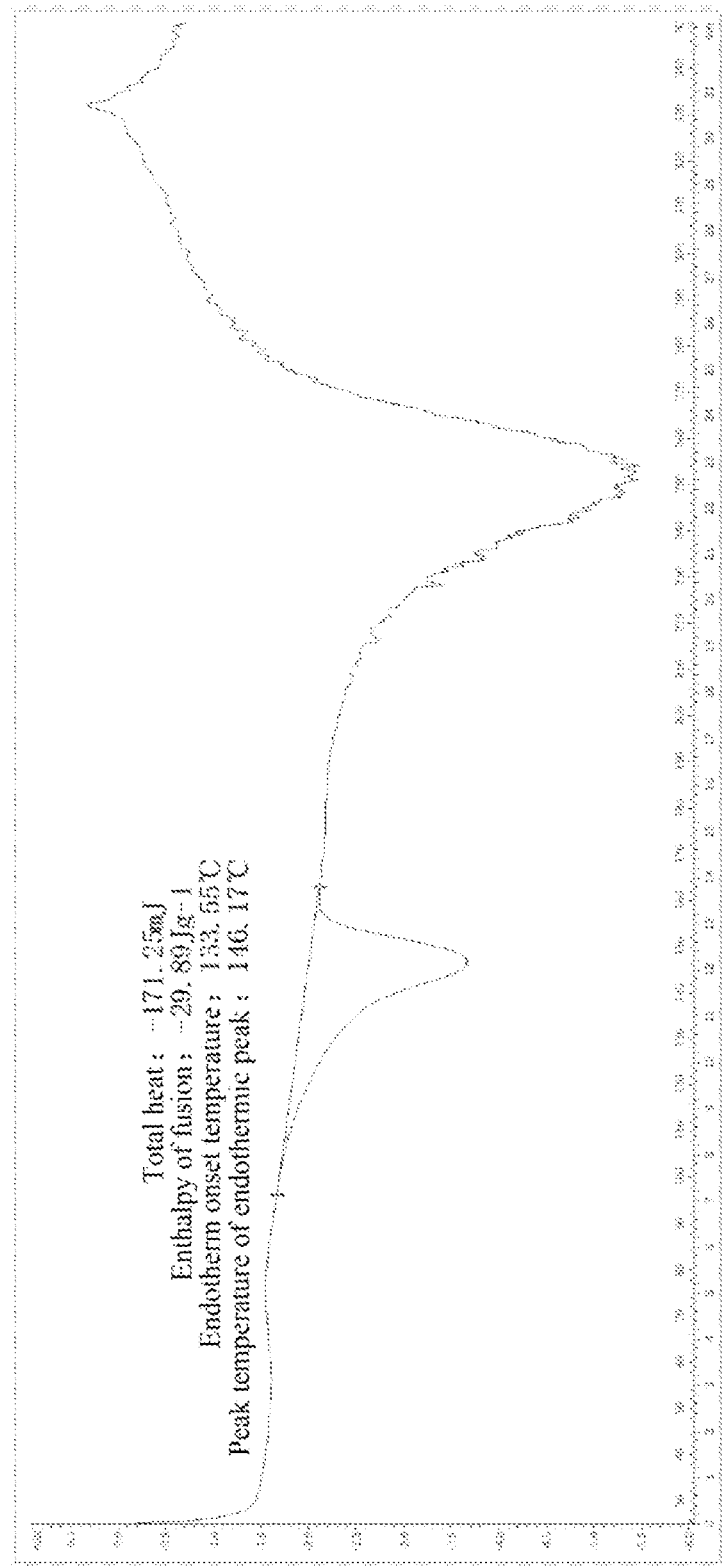
FIG. 8 is the DSC diagram of the compound of formula (I) present in crystal form B.
Figure 9:
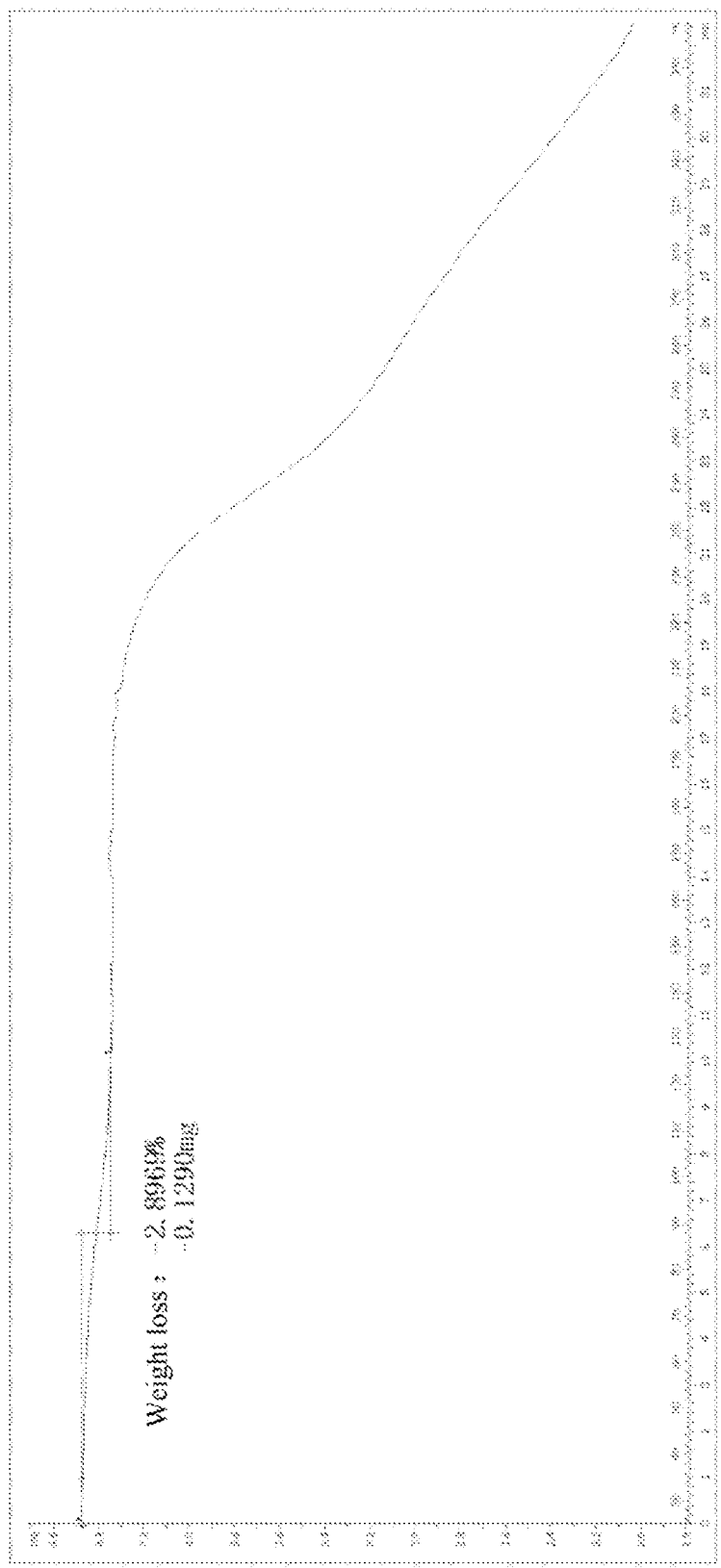
FIG. 9 is the TGA diagram of the compound of formula (I) present in crystal form B.
Figure 10:
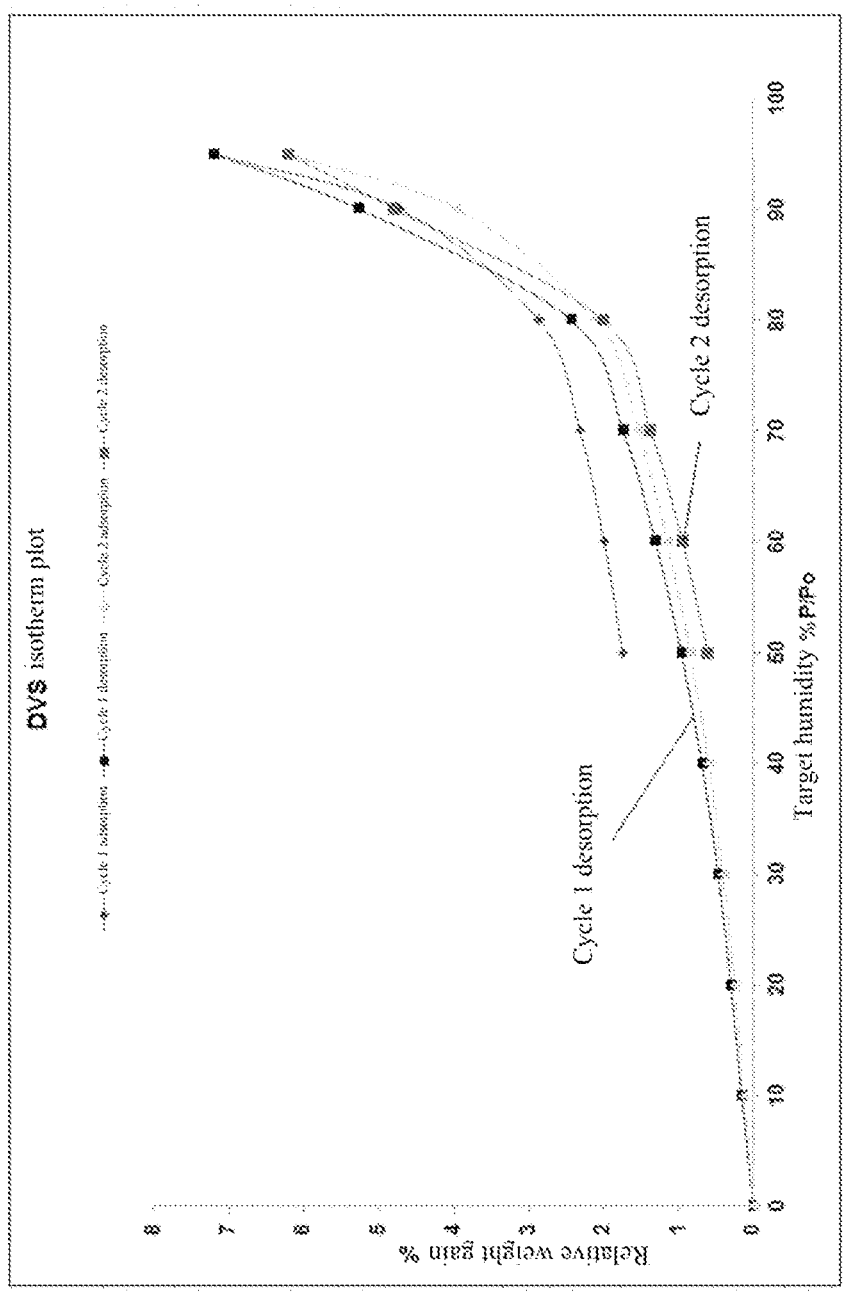
FIG. 10 is the DVS plot showing the hygroscopicity of the compound of formula (I) present in crystal form B.
Figure 11:
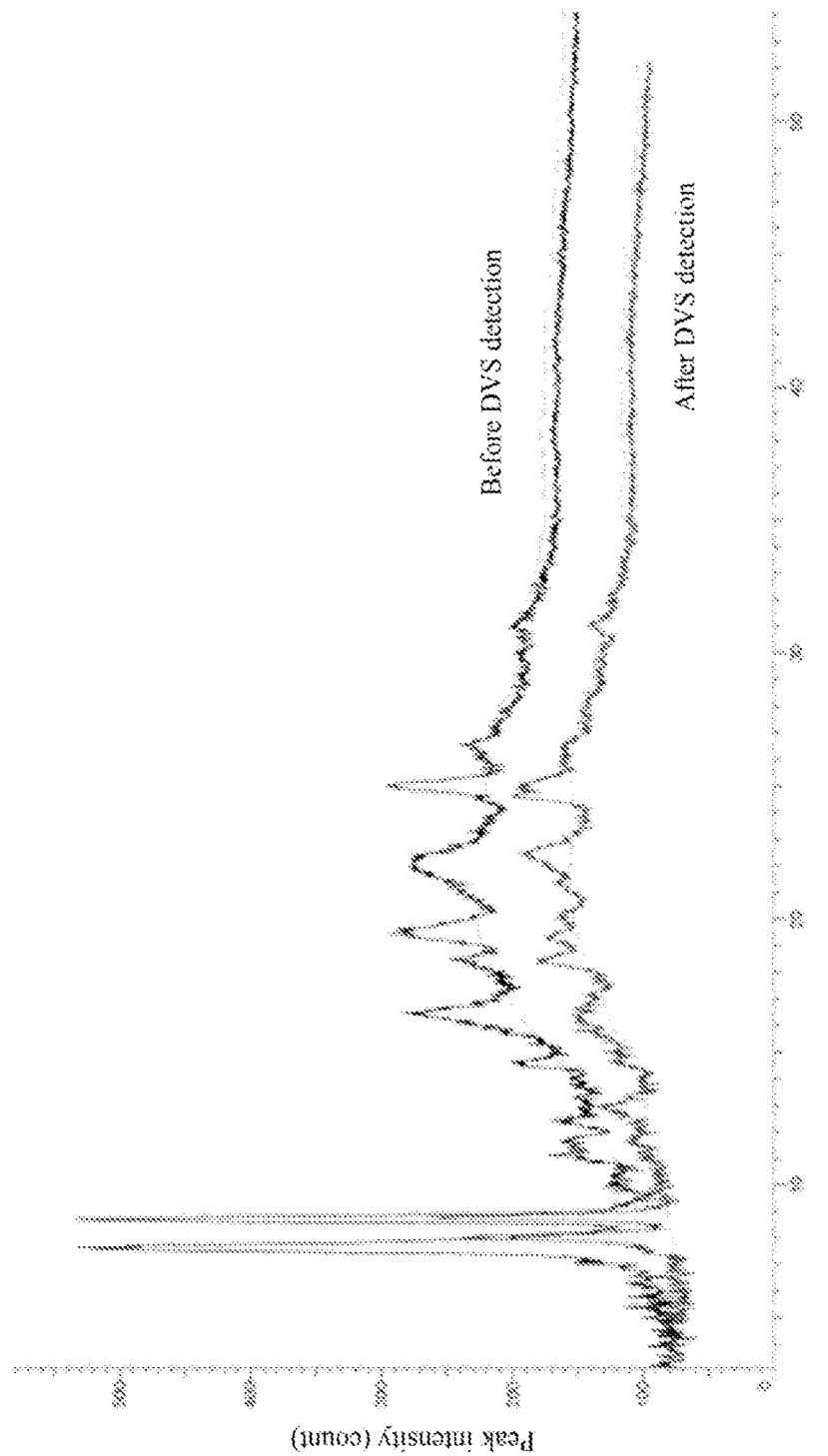
FIG. 11 is the XRPD pattern comparing the compound of formula (I) present in crystal form B before DVS detection and after DVS detection.

The DSC characterization is as shown in FIG. 8, with the peak temperature of the endothermic peak of 146.17° C. The TGA characterization is as shown in FIG. 9, with weight loss of 2.90% at 25° C. to 130° C. DVS characterization: According to the relative mass change curve, when the sample was stored at 25° C. and in the range of 10% RH to 80% RH, as the humidity increases, the mass was increased by about 1.968%, which was less than 2% but not less than 0.2%; and according to guidelines for drug hygroscopicity test in China Pharmacopoeia (2015 edition), the sample was slightly hygroscopic. When the sample was stored under normal conditions (i.e., 25° C. and 60% RH), the mass was increased by about 1.155%; when the sample was stored under accelerated test conditions (i.e., 70% RH), the mass was increased by about 1.530%; and when the sample was stored under extreme conditions (i.e., 90% RH), the mass was increased by about 3.963%. During a humidity change from 0% to 95%, the desorption process and adsorption process of the sample basically coincide. The DVS detection spectrum was as shown in FIG. 10, and the comparison for X-ray powder diffraction before and after DVS detection is as shown in FIG. 11, which indicates a change to crystal form A after DVS detection.

TABLE 2

Characteristic peaks of crystal form B

| Peak number | 2-Theta | d(A) | I% |
|---|---|---|---|
| Peak 1 | 7.620 | 11.593 | 100.0 |
| Peak 2 | 8.680 | 10.179 | 83.4 |
| Peak 3 | 11.042 | 8.006 | 8.6 |
| Peak 4 | 11.638 | 7.598 | 8.3 |
| Peak 5 | 12.339 | 7.167 | 9.2 |
| Peak 6 | 14.461 | 6.120 | 7.7 |

TABLE 2-continued

Characteristic peaks of crystal form B

| Peak number | 2-Theta | d(A) | I% |
|---|---|---|---|
| Peak 7 | 16.320 | 5.427 | 16.6 |
| Peak 8 | 18.123 | 4.891 | 6.1 |
| Peak 9 | 18.381 | 4.823 | 4.9 |
| Peak 10 | 19.381 | 4.576 | 15.3 |
| Peak 11 | 22.020 | 4.033 | 9.8 |
| Peak 12 | 25.038 | 3.554 | 14.4 |
| Peak 13 | 26.460 | 3.366 | 4.6 |

Example 9. Preparation of Crystal Form B

The compound of formula (I) (100 mg) was dissolved in 0.5 mL of tetrahydrofuran; and at room temperature, the solution was slowly added dropwise to 2 mL of isopropyl ether (containing about 4 mg of crystal seed A) with solid being precipitated, and stirred for another 16 hours. The reaction solution was filtered, and the filter cake was collected and dried in vacuum to obtain the product (35 mg). Detected by X-ray powder diffraction, the product was present in crystal form B.

Example 10. Preparation of Crystal Form B

The compound of formula (I) (100 mg) was added to 5 mL of methyl tert-butyl ether, which was undissolved; the mixture was slurried at room temperature for 24 hours and heated at 50° C. for 2 hours, same was undissolved; the mixture was then cooled to room temperature and centrifuged, and the solid sample was dried in vacuum to obtain the product. Detected by X-ray powder diffraction, the product was present in crystal form B.

Example 11. Preparation of Crystal Form B

The compound of formula (I) (100 mg) was added to 5 mL of cyclohexane, which was undissolved; the mixture was slurried at room temperature for 24 hours and heated at 50° C. for 2 hours, same was undissolved; the mixture was then cooled to room temperature and centrifuged, and the solid sample was dried in vacuum to obtain the product. Detected by X-ray powder diffraction, the product was present in crystal form B.

Example 12. Preparation of Crystal Form C

Figure 12:
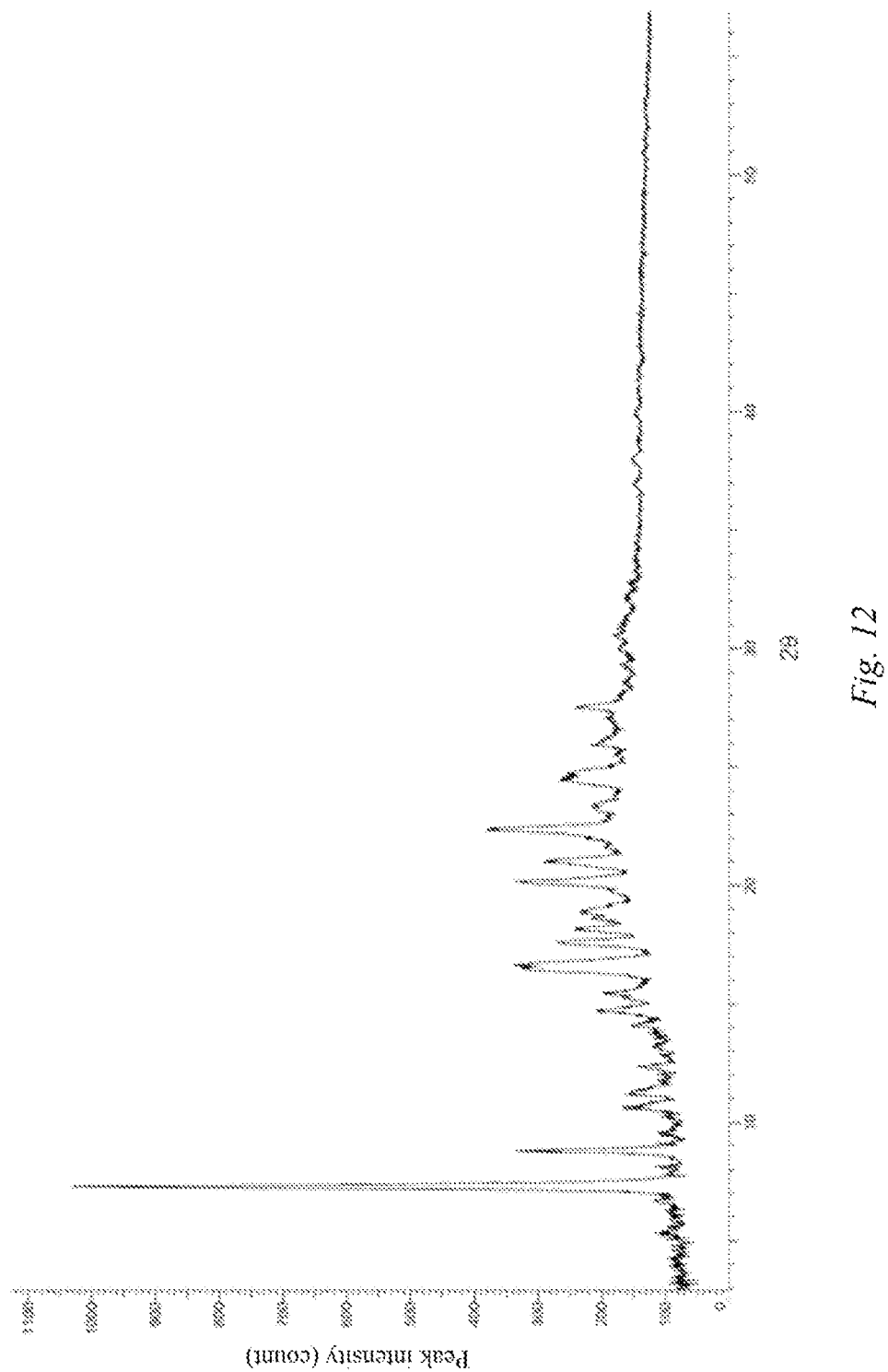
FIG. 12 is the XRPD pattern of the compound of formula (I) present in crystal form C.

The compound of formula (I) (100 mg) was added to 5 mL of p-xylene, which was undissolved; the mixture was slurried at room temperature for 24 hours and heated at 50° C. for 2 hours, same was undissolved; the mixture was then cooled to room temperature and centrifuged, and the solid sample was dried in vacuum to obtain the product. Detected by X-ray powder diffraction, the product was defined as crystal form C. The XRPD spectrum is as shown in FIG. 12.

Figure 13:
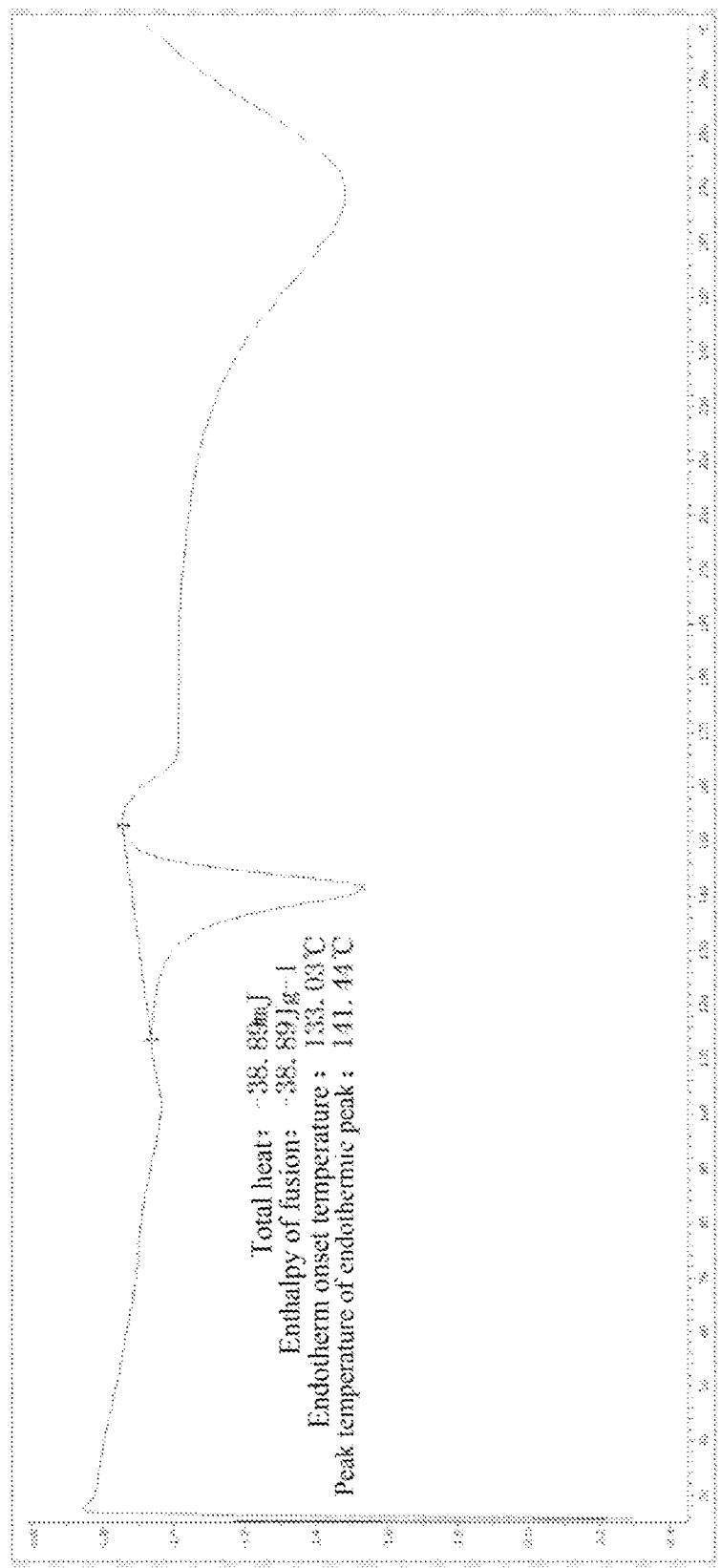
FIG. 13 is the DSC diagram of the compound of formula (I) present in crystal form C.
Figure 14:
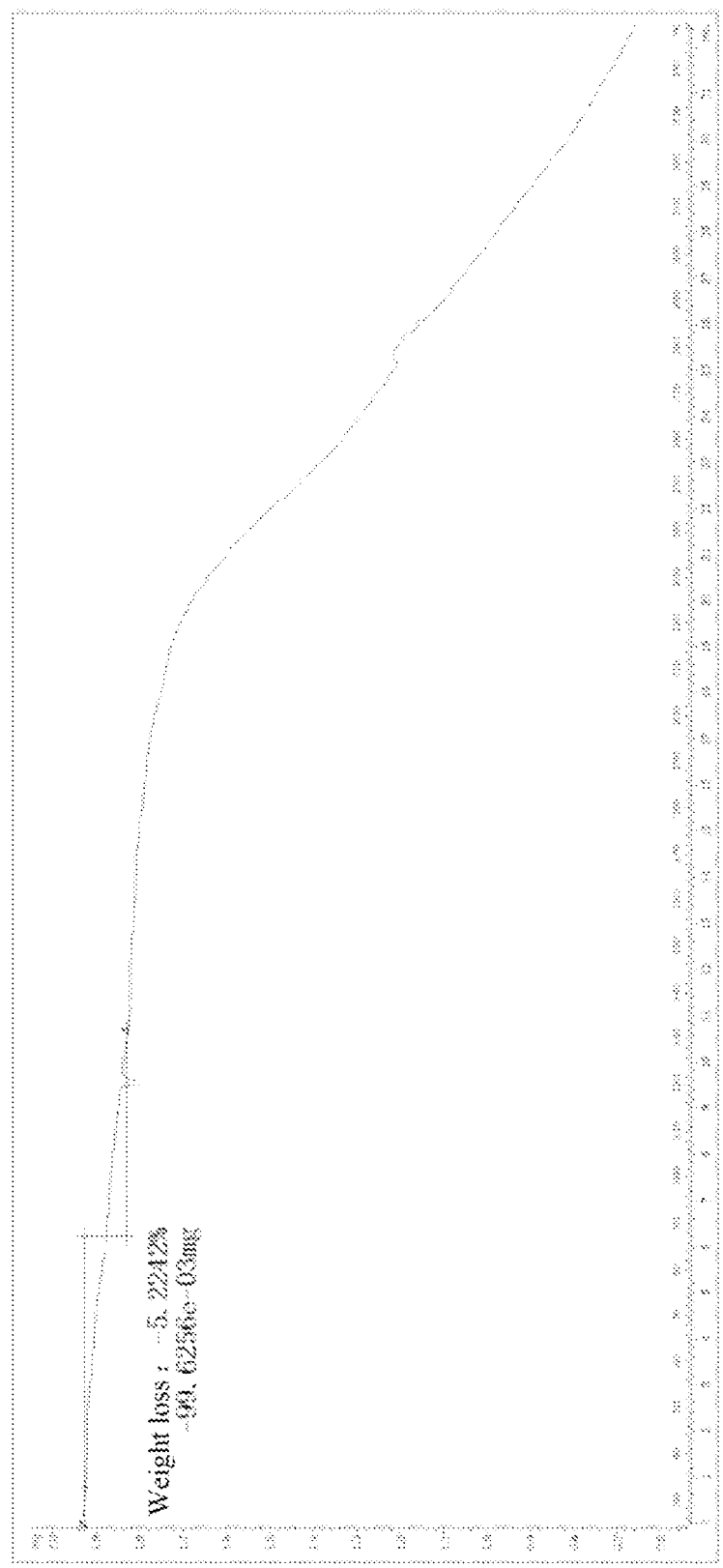
FIG. 14 is the TGA diagram of the compound of formula (I) present in crystal form C.

The DSC spectrum is as shown in FIG. 13, with the peak temperature of the endothermic peak of 141.44° C. The TGA spectrum is as shown in FIG. 14, with weight loss of 5.22% at 25° C. to 130° C.

TABLE 3

Characteristic peaks of crystal form C

| Peak number | 2-Theta | d(A) | I% |
|---|---|---|---|
| Peak 1 | 5.312 | 16.624 | 3.6 |
| Peak 2 | 6.704 | 13.173 | 3.8 |
| Peak 3 | 7.283 | 12.129 | 100.0 |
| Peak 4 | 8.780 | 10.063 | 28.7 |
| Peak 5 | 9.544 | 9.260 | 3.3 |
| Peak 6 | 10.664 | 8.289 | 9.0 |
| Peak 7 | 11.264 | 7.849 | 7.5 |
| Peak 8 | 12.335 | 7.170 | 4.4 |
| Peak 9 | 14.124 | 6.266 | 3.6 |
| Peak 10 | 14.744 | 6.004 | 9.7 |
| Peak 11 | 15.456 | 5.728 | 7.2 |
| Peak 12 | 16.587 | 5.340 | 18.8 |
| Peak 13 | 17.598 | 5.036 | 13.6 |
| Peak 14 | 18.165 | 4.880 | 9.1 |
| Peak 15 | 18.915 | 4.688 | 7.0 |
| Peak 16 | 20.158 | 4.402 | 17.4 |
| Peak 17 | 21.025 | 4.222 | 11.8 |
| Peak 18 | 22.363 | 3.972 | 19.9 |
| Peak 19 | 23.211 | 3.829 | 2.4 |
| Peak 20 | 24.504 | 3.630 | 7.6 |
| Peak 21 | 24.713 | 3.600 | 7.5 |
| Peak 22 | 26.042 | 3.419 | 3.1 |
| Peak 23 | 27.534 | 3.237 | 7.9 |

Example 13. Preparation of Crystal Form D

Figure 15:
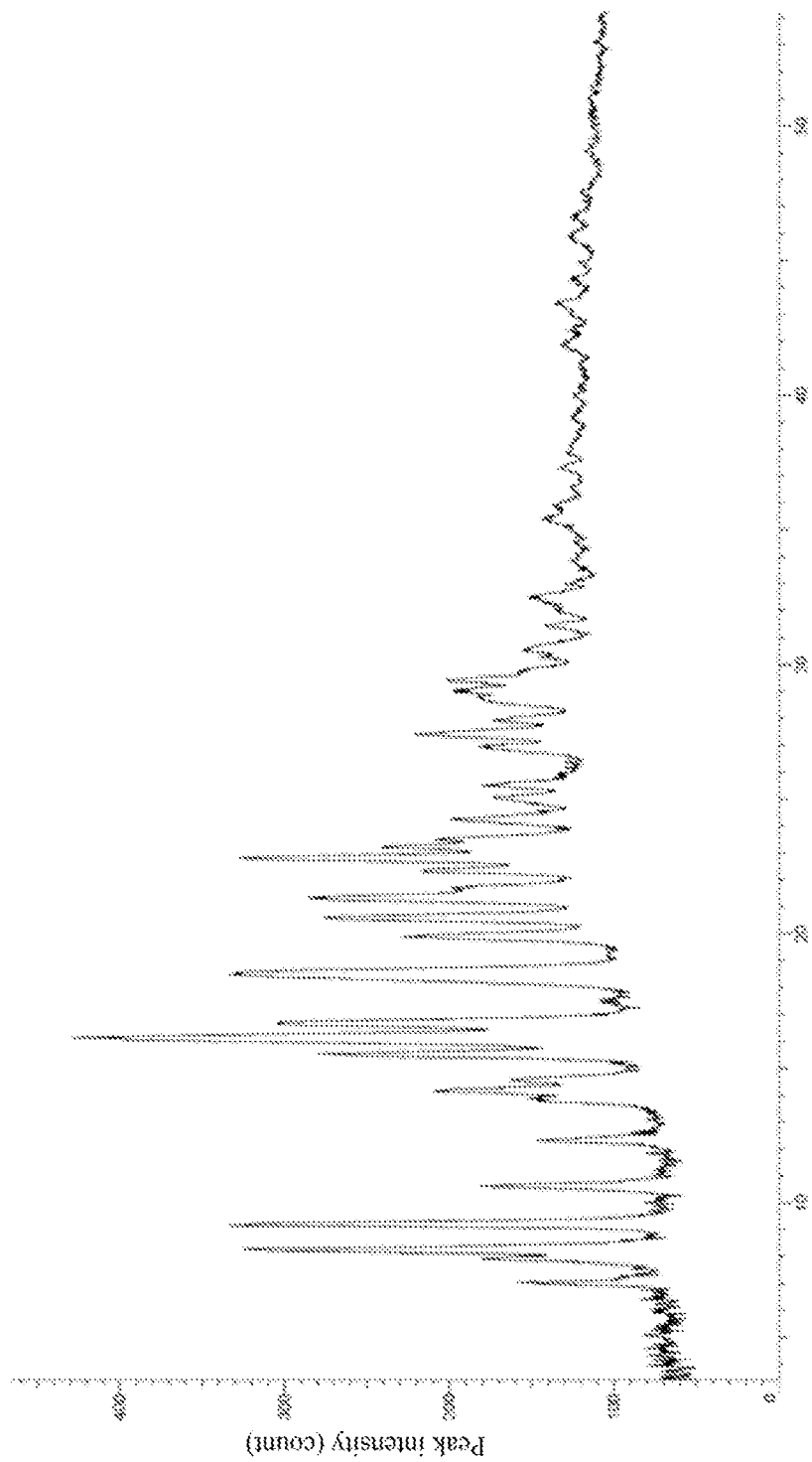
FIG. 15 is the XRPD pattern of the compound of formula (I) present in crystal form D.

The compound of formula (I) (1.7 g) was added to 3.4 mL of ethyl acetate, heated to 80° C., stirred until the solution was clear, stirred for another 1 hours with solid being precipitated, slowly cooled to 15° C. and stirred for another 4 hours at 15° C. The reaction solution was filtered, and the filter cake was collected and dried in vacuum to obtain the product (1.5 g). Detected by X-ray powder diffraction, the product was defined as crystal form D. The spectrum is as shown in FIG. 15.

Figure 16:
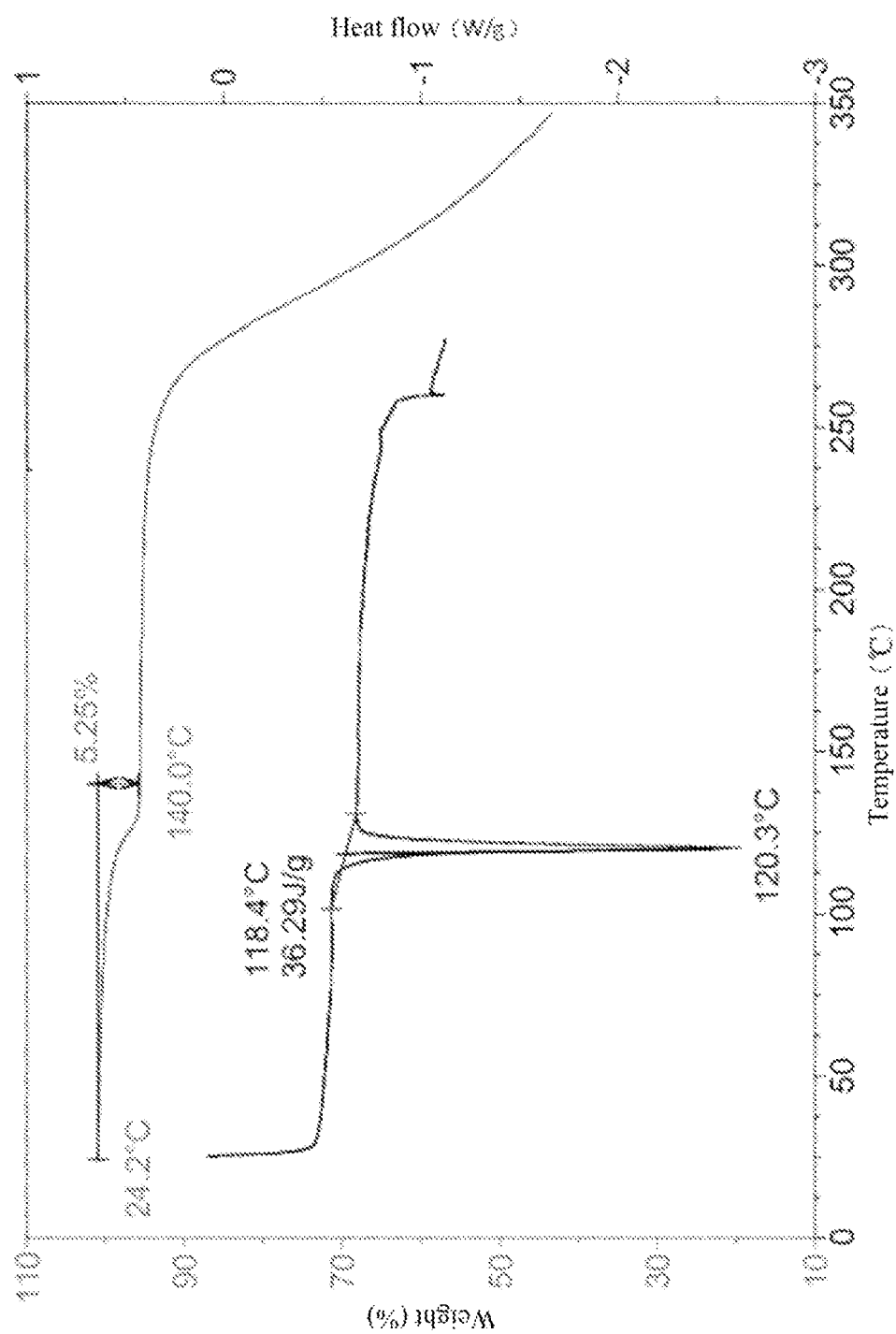
FIG. 16 is the DSC and TGA diagram of the compound of formula (I) present in crystal form D.

The DSC spectrum and TGA spectrum are as shown in FIG. 16, with the peak temperature of the endothermic peak of 118.4° C. in the DSC spectrum and weight loss of 5.25% at 24.2° C. to 140° C. in the TGA spectrum.

Figure 17:
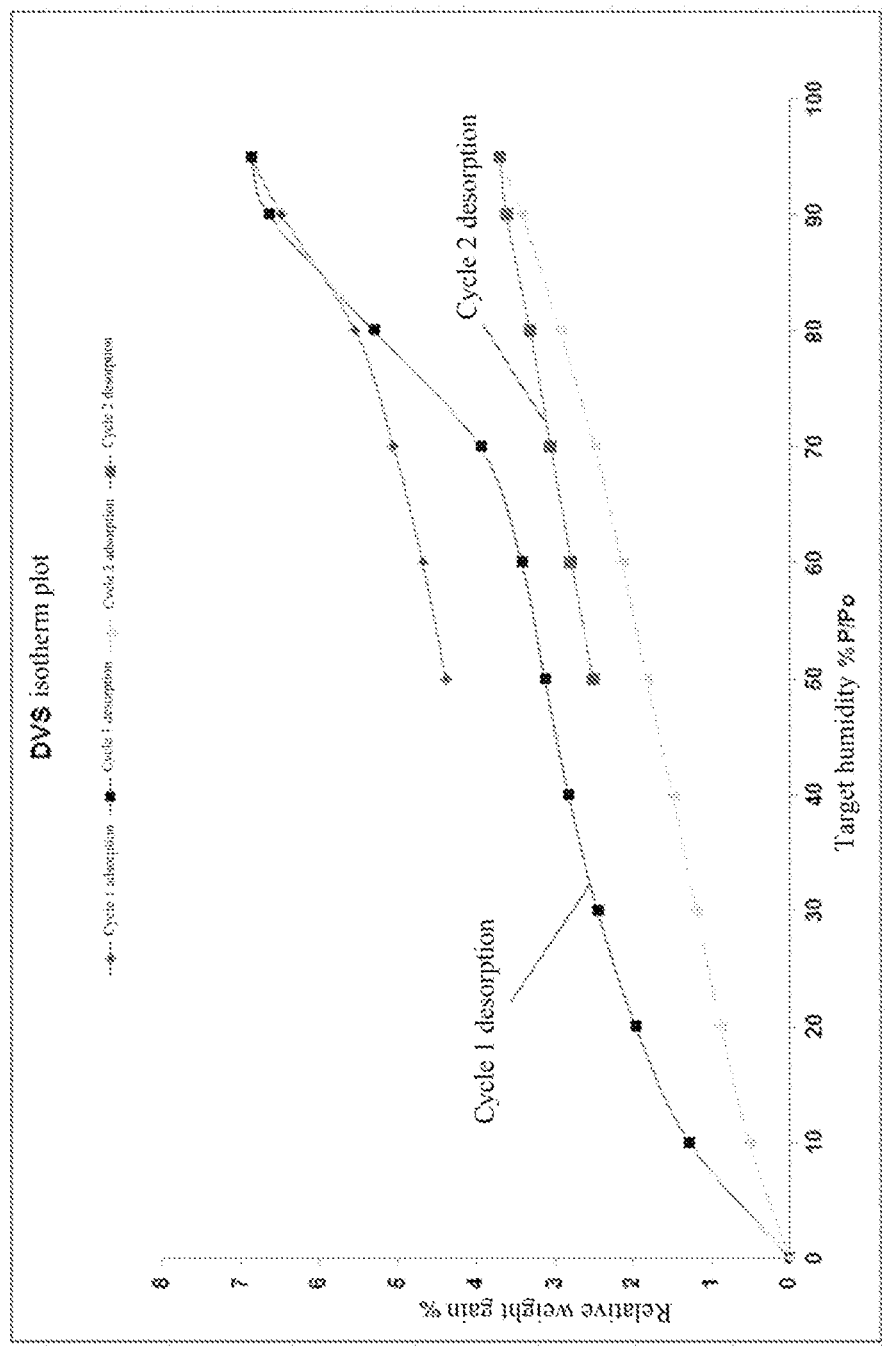
FIG. 17 is the DVS plot showing the hygroscopicity of the compound of formula (I) present in crystal form D.
Figure 18:
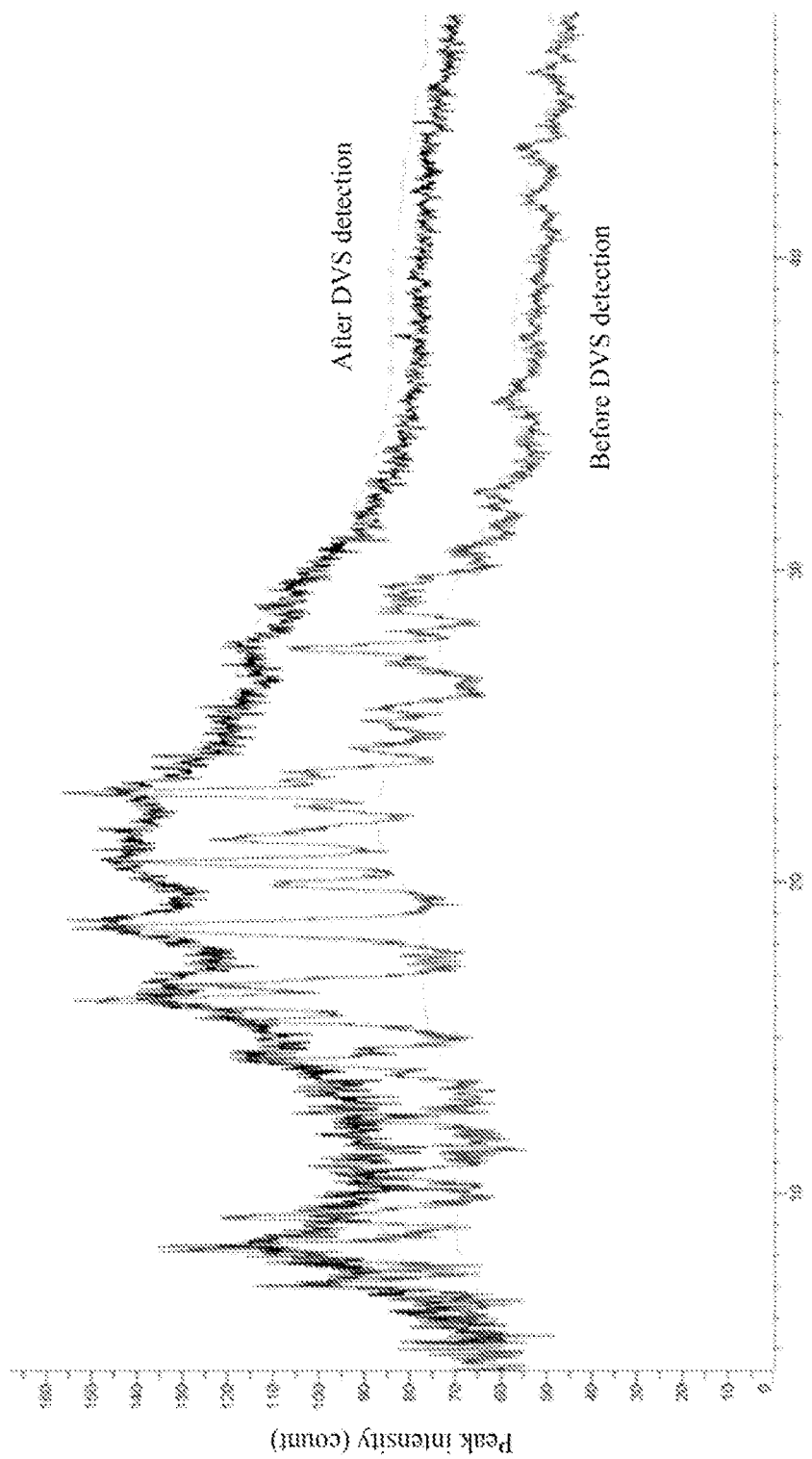
FIG. 18 is the XRPD pattern comparing the compound of formula (I) present in crystal form D before DVS detection and after DVS detection.

DVS characterization: According to the relative mass change curve, when the sample was stored at 25° C. and in the range of 10% RH to 80% RH, as the humidity increases, the mass was increased by about 2.420%, which was less than 15% but not less than 2%; and according to guidelines for drug hygroscopicity test in China Pharmacopoeia (2015 edition), the sample was hygroscopic. When the sample was stored under normal conditions (i.e., 25° C. and 60% RH), the mass was increased by about 2.143%; when the sample was stored under accelerated test conditions (i.e., 70% RH), the mass was increased by about 2.494%; and when the sample was stored under extreme conditions (i.e., 90% RH), the mass was increased by about 3.422%. During a humidity change from 0% to 95%, the desorption process and adsorption process of the sample do not coincide. The DVS detection spectrum is as shown in FIG. 17, and the comparison for X-ray powder diffraction before and after DVS detection is as shown in FIG. 18, which indicates that the crystallinity of the crystal form become worse after DVS detection.

TABLE 4

Characteristic peaks of crystal form D

| Peak number | 2-Theta | d(A) | I% |
|---|---|---|---|
| Peak 1 | 7.021 | 12.581 | 23.1 |
| Peak 2 | 7.901 | 11.181 | 31.2 |
| Peak 3 | 8.259 | 10.696 | 76.3 |
| Peak 4 | 9.200 | 9.605 | 78.8 |
| Peak 5 | 10.639 | 8.308 | 34.0 |
| Peak 6 | 12.320 | 7.178 | 22.7 |
| Peak 7 | 13.821 | 6.402 | 19.6 |
| Peak 8 | 14.180 | 6.241 | 38.9 |
| Peak 9 | 14.580 | 6.070 | 22.7 |
| Peak 10 | 15.519 | 5.705 | 41.7 |
| Peak 11 | 16.120 | 5.494 | 100.0 |
| Peak 12 | 16.661 | 5.317 | 58.9 |
| Peak 13 | 18.500 | 4.792 | 72.3 |
| Peak 14 | 19.919 | 4.454 | 33.3 |
| Peak 15 | 20.600 | 4.308 | 47.0 |
| Peak 16 | 21.320 | 4.164 | 48.0 |
| Peak 17 | 21.700 | 4.092 | 20.2 |
| Peak 18 | 22.358 | 3.973 | 19.9 |
| Peak 19 | 22.820 | 3.894 | 60.4 |
| Peak 20 | 23.221 | 3.827 | 30.5 |
| Peak 21 | 23.538 | 3.777 | 19.3 |
| Peak 22 | 24.241 | 3.669 | 20.2 |
| Peak 23 | 25.060 | 3.551 | 13.1 |
| Peak 24 | 25.520 | 3.488 | 14.3 |
| Peak 25 | 26.920 | 3.309 | 12.1 |
| Peak 26 | 27.420 | 3.250 | 28.3 |
| Peak 27 | 27.940 | 3.191 | 10.6 |
| Peak 28 | 28.720 | 3.106 | 13.1 |
| Peak 29 | 29.020 | 3.074 | 19.9 |
| Peak 30 | 29.420 | 3.034 | 20.9 |
| Peak 31 | 30.560 | 2.923 | 9.3 |
| Peak 32 | 31.402 | 2.846 | 7.2 |
| Peak 33 | 32.460 | 2.756 | 10.0 |
| Peak 34 | 35.380 | 2.535 | 6.5 |
| Peak 35 | 35.919 | 2.498 | 4.4 |
| Peak 36 | 37.261 | 2.411 | 4.0 |

Example 14. Preparation of Crystal Form D

The compound of formula (I) (1 g) was added to 4.5 mL of ethyl acetate, heated to 80° C., stirred until the solution was clear, slowly added dropwise with 4 mL of n-hexane at 80° C. with no solid being precipitated, slowly cooled to 70° C. with solid being precipitated, slowly cooled to 20° C. (about 5 hours) and stirred at 20° C. for another 15 hours. The reaction solution was filtered, and the filter cake was collected and dried in vacuum to obtain the product (0.89 g). Detected by X-ray powder diffraction, the product was present in crystal form D.

Example 15. Preparation of Crystal Form D

The compound of formula (I) (200 mg) was added to 2 mL of acetone, heated to 50° C., stirred until the solution was clear, slowly added dropwise with 3.5 mL of n-heptane with no solid being precipitated, slowly cooled to 20° C. with solution being turbid, slowly cooled to 15° C. to 20° C. and stirred for another 16 hours. The reaction solution was filtered, and the filter cake was collected and dried in vacuum to obtain the product (130 mg). Detected by X-ray powder diffraction, the product was present in crystal form D.

Example 16. Preparation of Crystal Form D

The compound of formula (I) (100 mg) was dissolved in 1 mL of ethyl acetate, slowly added dropwise with 2 mL of n-hexane (containing about 4 mg of crystal seeds of crystal form A, at 15° C. to 20° C.) with solid being precipitated, and stirred for another 3 hours. The reaction solution was filtered, and the filter cake was collected and dried in vacuum to obtain the product (35 mg). Detected by X-ray powder diffraction, the product was present in crystal form D.

Example 17. Preparation of Crystal Form D

The compound of formula (I) (100 mg) was dissolved in 0.5 mL of acetone, slowly added dropwise with 2 mL of isopropyl ether (containing about 4 mg of crystal seeds of crystal form A, at 15° C. to 20° C.) with solid being precipitated, and stirred for another 5 hours. The reaction solution was filtered, and the filter cake was collected and dried in vacuum to obtain the product (60 mg). Detected by X-ray powder diffraction, the product was present in crystal form D.

Example 18. Preparation of Crystal Form D

Figure 19:
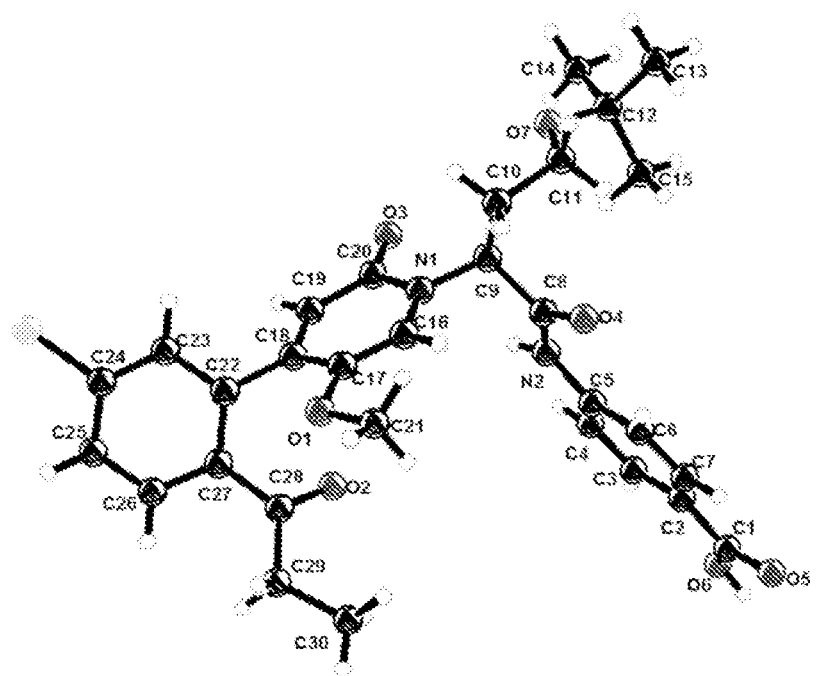
FIG. 19 is the ellipsoid diagram for single crystal analysis of molecular stereochemical structure of the compound of formula (I) present in crystal form D.

The compound of formula (I) (60 mg) was dissolved in 0.8 mL of a mixed solvent of acetone and isopropyl ether (V:V=1:3), filtered through a filtration membrane and covered with PE membrane, in which holes were punctured for slow volatilization, with cubic particles being precipitated; the samples were taken and the ellipsoid diagram for single crystal analysis of molecular stereochemical structure is as shown in FIG. 19. Detected by X-ray powder diffraction, the product was present in crystal form D.

Example 19. Preparation of Crystal Form E

Figure 20:
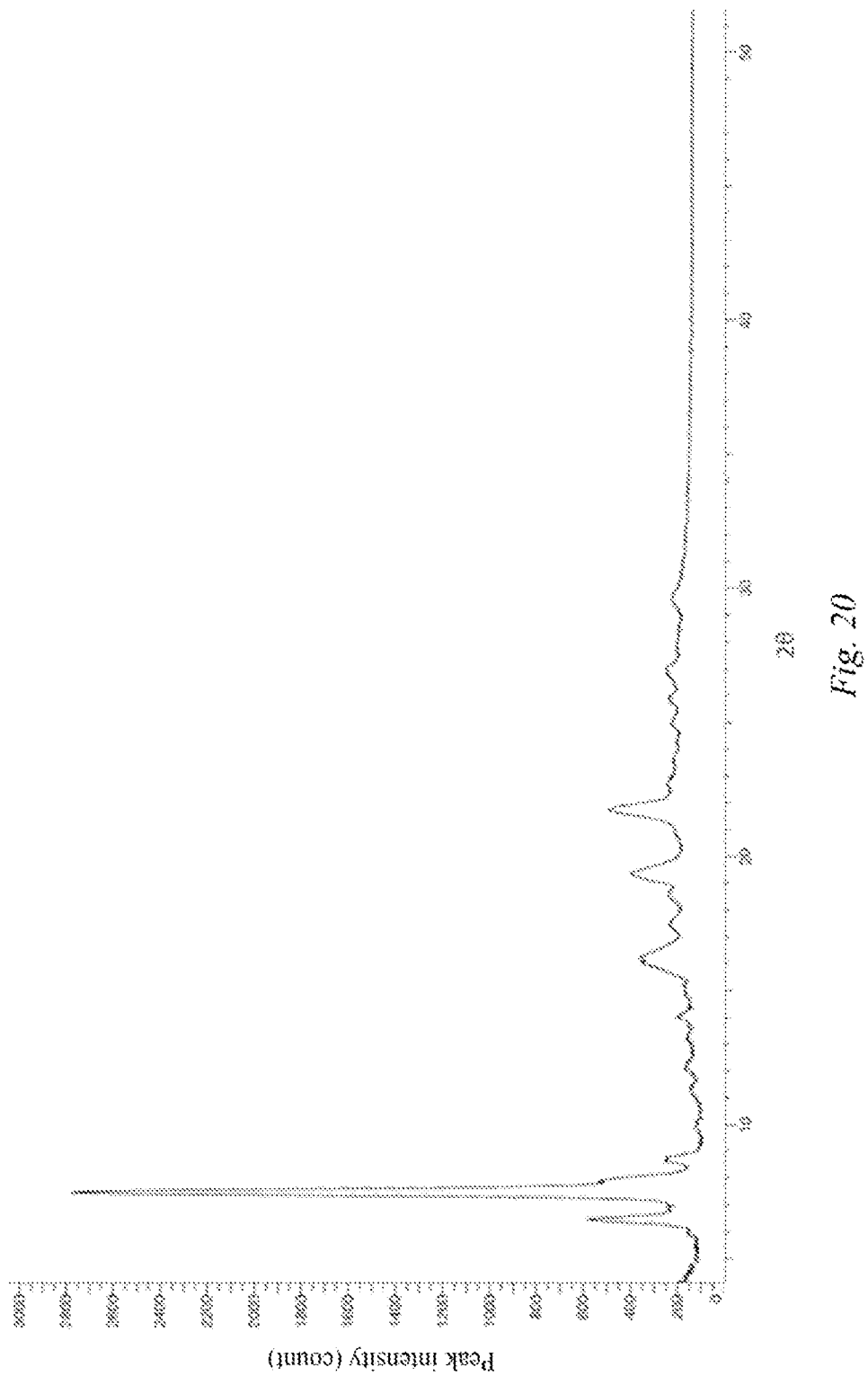
FIG. 20 is the XRPD pattern of the compound of formula (I) present in crystal form E.

The compound of formula (I) (20 mg) was dissolved in 0.5 mL of a mixed solvent of acetone and cyclohexane (V:V=1:3), filtered through a filtration membrane and covered with PE membrane, in which holes were punctured for slow volatilization naturally, and a solid was precipitated; the reaction solution was filtered, and the filter cake was collected and dried in vacuum to obtain the product (8 mg). Detected by X-ray powder diffraction, the product was defined as crystal form E. The spectrum is as shown in FIG. 20.

TABLE 5

Characteristic peaks of crystal form E

| Peak number | 2-Theta | d(A) | I% |
|---|---|---|---|
| Peak 1 | 6.460 | 13.671 | 14.7 |
| Peak 2 | 7.480 | 11.810 | 100.0 |
| Peak 3 | 7.977 | 11.074 | 11.6 |
| Peak 4 | 8.662 | 10.200 | 3.9 |
| Peak 5 | 11.299 | 7.825 | 1.2 |
| Peak 6 | 12.140 | 7.285 | 1.6 |
| Peak 7 | 14.038 | 6.303 | 2.0 |
| Peak 8 | 16.220 | 5.460 | 7.1 |
| Peak 9 | 17.440 | 5.081 | 1.7 |
| Peak 10 | 18.560 | 4.777 | 1.2 |
| Peak 11 | 19.360 | 4.581 | 7.9 |
| Peak 12 | 21.720 | 4.088 | 10.6 |
| Peak 13 | 22.664 | 3.920 | 0.7 |
| Peak 14 | 24.922 | 3.570 | 1.1 |
| Peak 15 | 25.940 | 3.432 | 1.2 |
| Peak 16 | 26.840 | 3.319 | 1.6 |
| Peak 17 | 29.620 | 3.014 | 1.6 |

Example 20. Preparation of Crystal Form F

Figure 21:
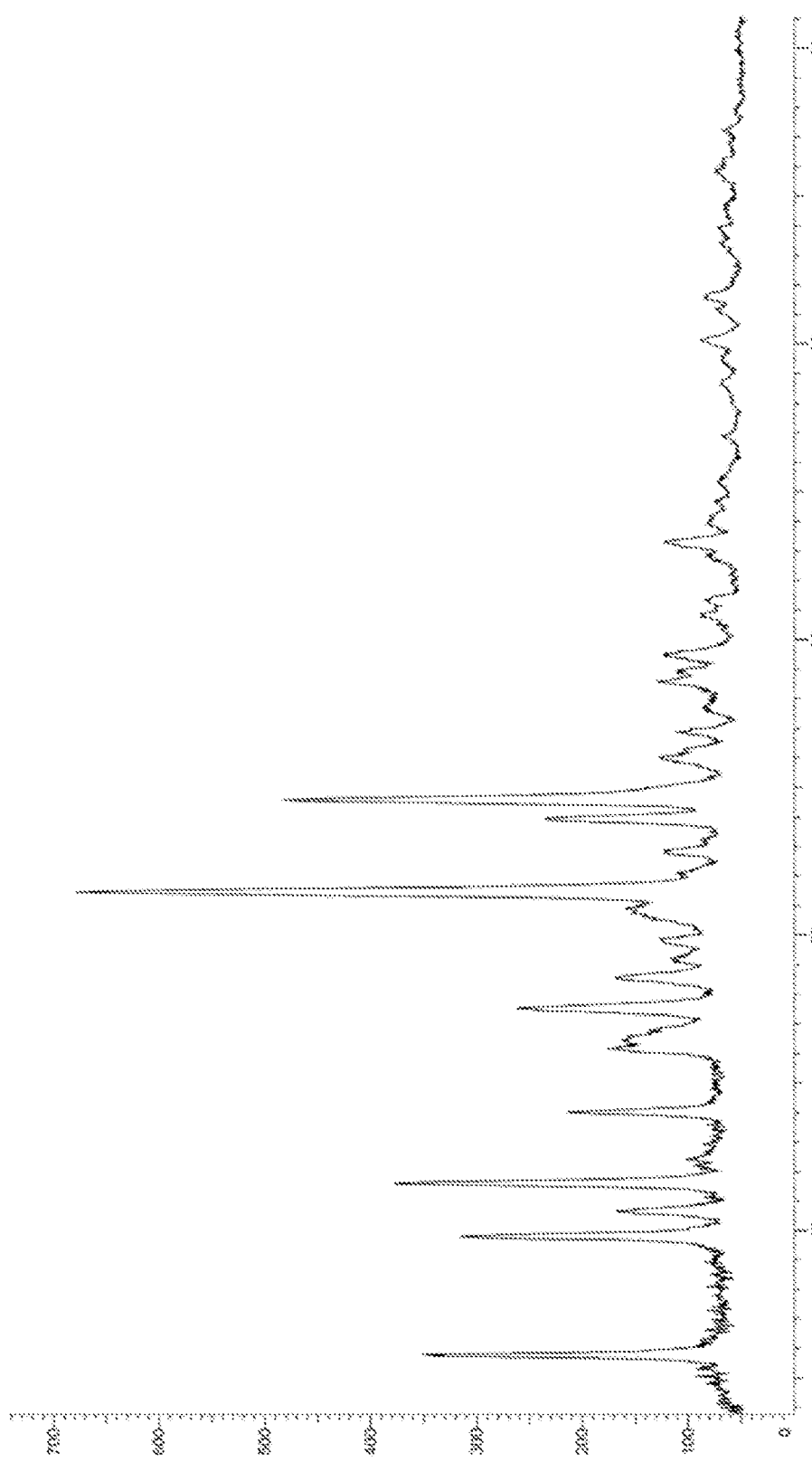
FIG. 21 is the XRPD pattern of the compound of formula (I) present in crystal form F.

The compound of formula (I) (1 g) was added to 3 mL of ethyl acetate, heated to 80° C., stirred until the solution was clear, stirred for another 30 minutes with solid being precipitated, slowly added dropwise with 4.5 mL of n-hexane at 80° C., slowly cooled to 20° C. (about 3 hours) and stirred for another 3 hours at 20° C. The reaction solution was filtered, and the filter cake was collected and dried in vacuum to obtain the product (855 mg). Detected by X-ray powder diffraction, the product was defined as crystal form F. The spectrum is as shown in FIG. 21.

Figure 22:
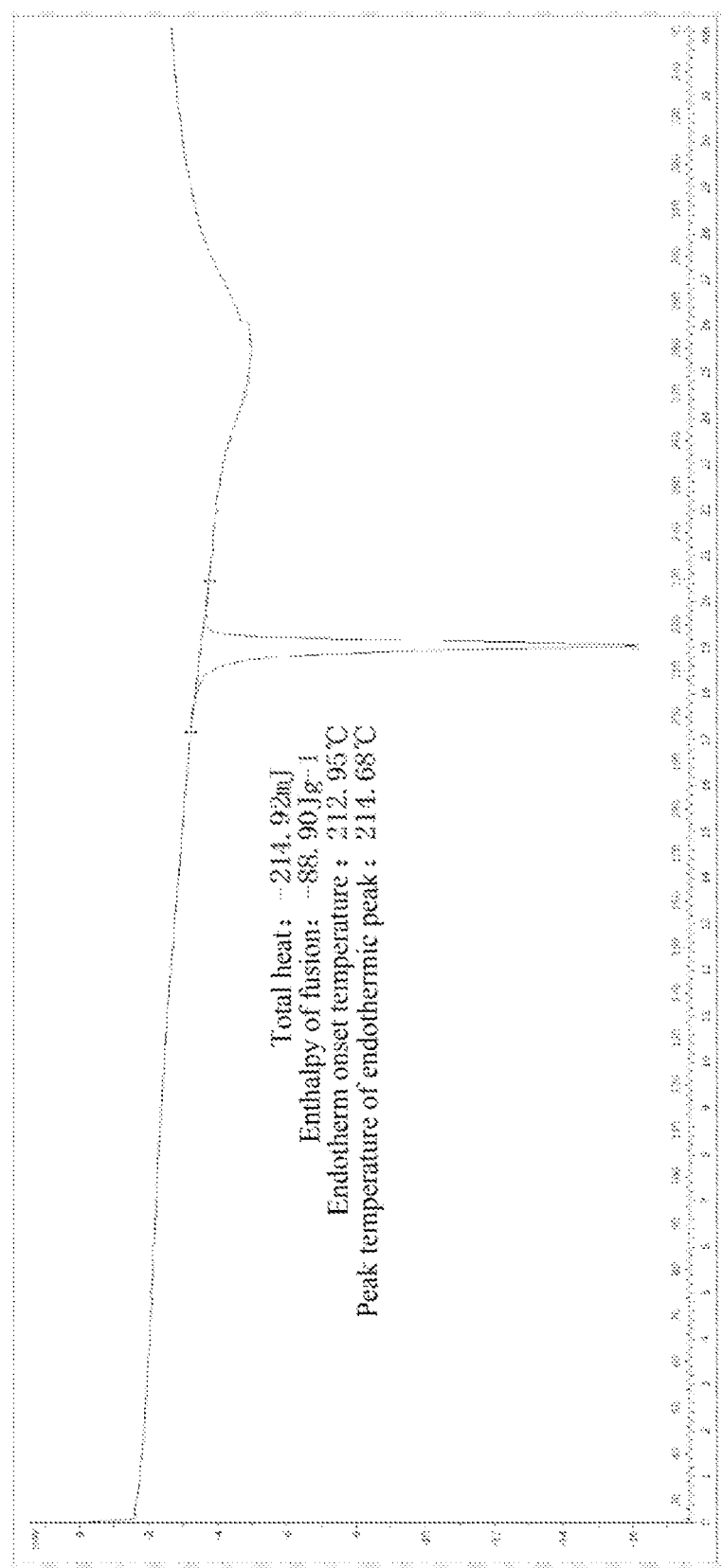
FIG. 22 is the DSC diagram of the compound of formula (I) present in crystal form F.
Figure 23:
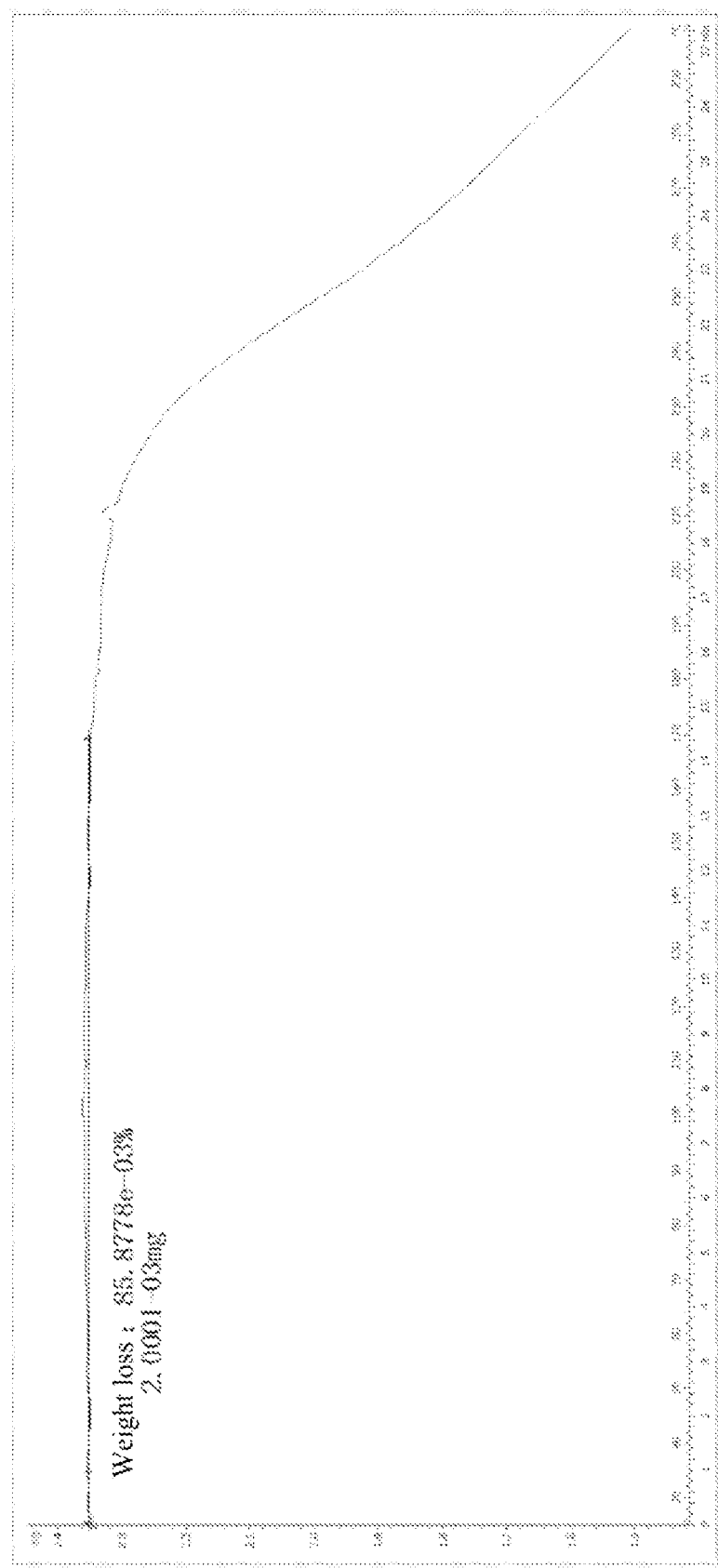
FIG. 23 is the TGA diagram of the compound of formula (I) present in crystal form F.

The DSC spectrum is as shown in FIG. 22, with the peak temperature of the endothermic peak of 214.68° C. The TGA spectrum is as shown in FIG. 23.

Figure 24:
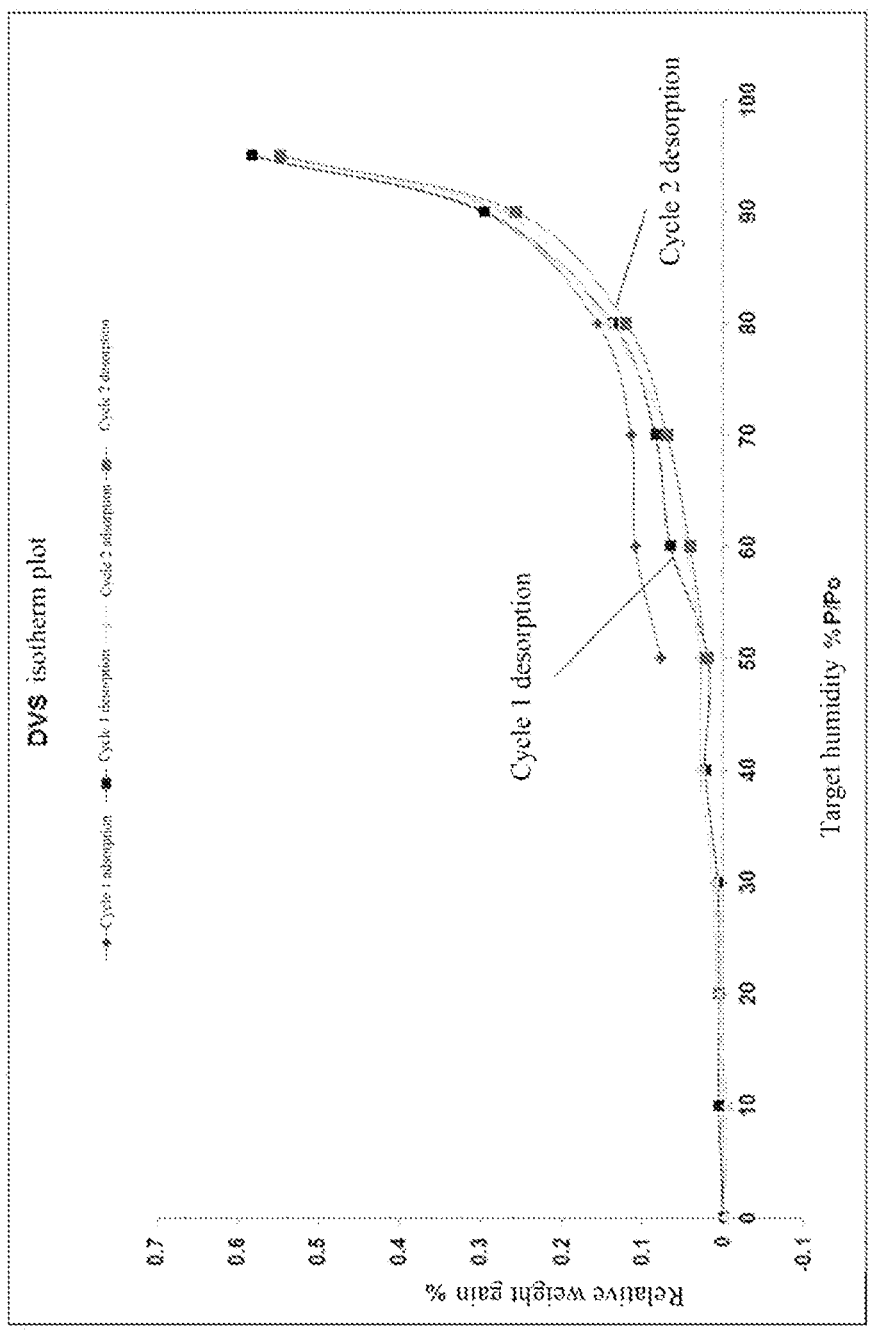
FIG. 24 is the DVS plot showing the hygroscopicity of the compound of formula (I) present in crystal form F.
Figure 25:
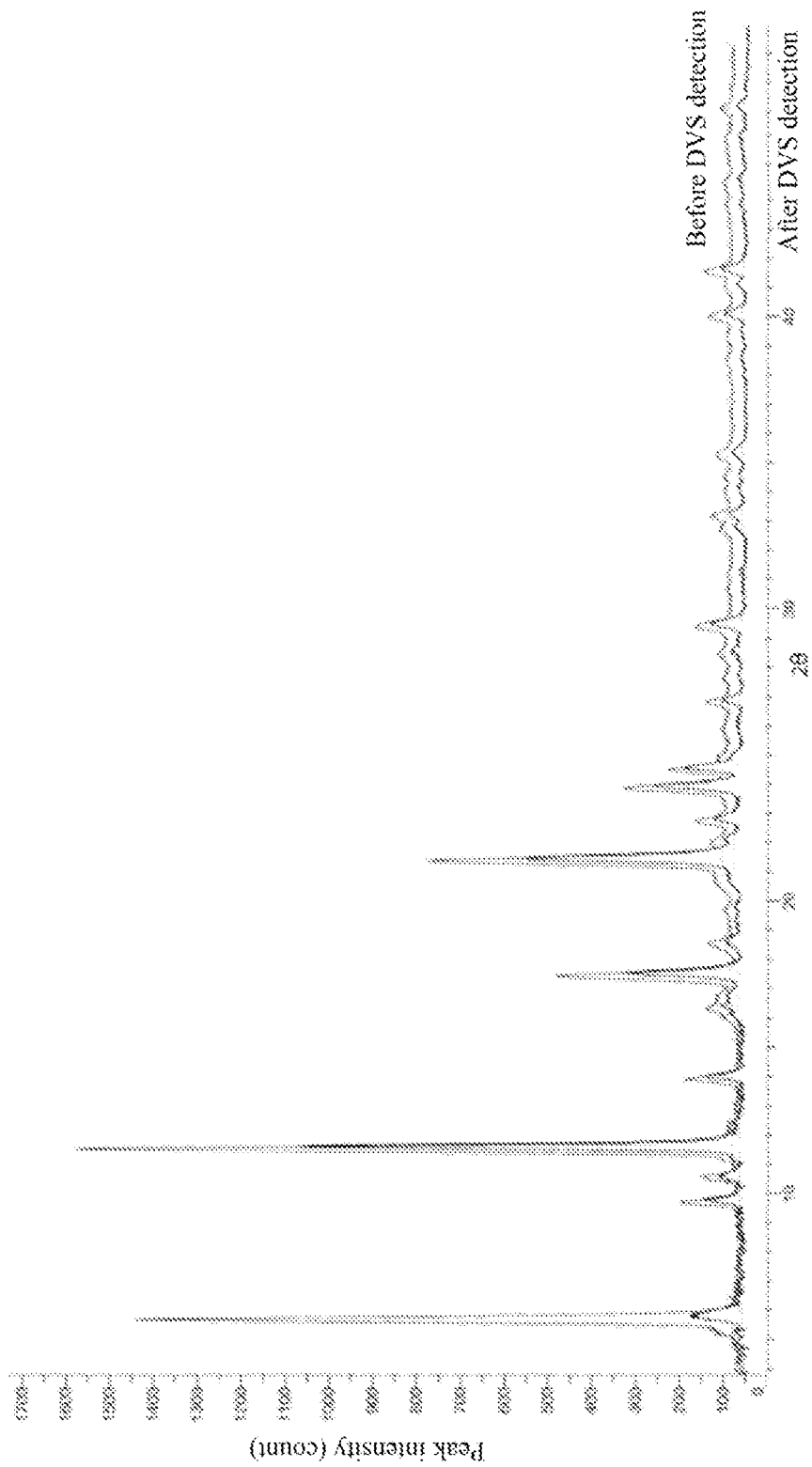
FIG. 25 is the XRPD pattern comparing the compound of formula (I) present in crystal form F before DVS detection and after DVS detection.

DVS characterization: According to the relative mass change curve, when the sample was stored at 25° C. and in the range of 10% RH to 80% RH, as the humidity increases, the mass was increased by about 0.1464%, which less than 2%; and according to guidelines for drug hygroscopicity test in China Pharmacopoeia (2015 edition), the sample was hardly hygroscopic. When the sample was stored under normal conditions (i.e., 25° C. and 60% RH), the mass was increased by about 0.0457%; when the sample was stored under accelerated test conditions (i.e., 70% RH), the mass was increased by about 0.0701%; and when the sample was stored under extreme conditions (i.e., 90% RH), the mass was increased by about 0.2744%. During a humidity change from 0% to 95%, the desorption process and adsorption process of the sample basically coincide, and the crystal form was unchanged before and after DVS detection. The DVS curve is as shown in FIG. 24, and the comparison for X-ray powder diffraction before and after DVS detection is as shown in FIG. 25.

TABLE 6

Characteristic peaks of crystal form F

| Peak number | 2-Theta | d(A) | I% |
|---|---|---|---|
| Peak 1 | 5.761 | 15.329 | 46.9 |
| Peak 2 | 9.800 | 9.018 | 41.5 |
| Peak 3 | 10.640 | 8.308 | 15.7 |
| Peak 4 | 11.621 | 7.609 | 51.6 |
| Peak 5 | 14.021 | 6.311 | 23.9 |
| Peak 6 | 16.180 | 5.474 | 15.3 |
| Peak 7 | 16.460 | 5.381 | 12.9 |
| Peak 8 | 16.740 | 5.292 | 7.7 |
| Peak 9 | 17.520 | 5.058 | 29.6 |
| Peak 10 | 18.560 | 4.777 | 14.1 |
| Peak 11 | 19.142 | 4.633 | 4.7 |
| Peak 12 | 19.820 | 4.476 | 6.4 |
| Peak 13 | 21.460 | 4.137 | 100.0 |
| Peak 14 | 22.820 | 3.894 | 8.2 |
| Peak 15 | 23.939 | 3.714 | 25.8 |
| Peak 16 | 24.580 | 3.619 | 70.0 |
| Peak 17 | 25.981 | 3.427 | 9.2 |
| Peak 18 | 26.280 | 3.388 | 6.4 |
| Peak 19 | 26.861 | 3.316 | 6.6 |
| Peak 20 | 27.700 | 3.218 | 2.8 |
| Peak 21 | 28.580 | 3.121 | 8.0 |
| Peak 22 | 28.921 | 3.085 | 6.6 |
| Peak 23 | 29.480 | 3.028 | 8.0 |
| Peak 24 | 30.840 | 2.897 | 5.1 |
| Peak 25 | 31.340 | 2.852 | 3.8 |
| Peak 26 | 32.801 | 2.728 | 3.5 |
| Peak 27 | 33.300 | 2.688 | 9.9 |
| Peak 28 | 33.921 | 2.641 | 2.6 |
| Peak 29 | 35.321 | 2.539 | 1.9 |
| Peak 30 | 36.843 | 2.438 | 2.3 |
| Peak 31 | 38.660 | 2.327 | 2.1 |
| Peak 32 | 40.101 | 2.247 | 5.4 |
| Peak 33 | 41.121 | 2.193 | 2.8 |
| Peak 34 | 41.600 | 2.169 | 5.6 |

Example 21. Preparation of Crystal Form F

The compound of formula (I) (12 g) was added to 240 mL of ethyl formate, heated to internal temperature of 54° C. to reflux and stirred until the solution was clear; 300 mL of n-hexane was slowly added dropwise under refluxing conditions to obtain a clear solution, which was then added with crystal seeds of crystal form F under refluxing conditions, with solid being undissolved; the solution was stirred for another 30 minutes under refluxing conditions, with solid being precipitated slowly, slowly cooled to room temperature and stirred for another 16 hours. The reaction solution was filtered, and the filter cake was collected and dried in vacuum to obtain the product (8.2 g). Detected by X-ray powder diffraction, the product was present in crystal form F.

Example 22. Preparation of Crystal Form A

Crystal form B of the compound of formula (I) (25 mg) was added to 0.4 mL of toluene, slurried and stirred for 90 hours at room temperature. The reaction solution was filtered, and the filter cake was collected and dried in vacuum to obtain the product (13 mg). Detected by X-ray powder diffraction, the product was present in crystal form A.

Example 23. Preparation of Crystal Form A

Crystal form B of the compound of formula (I) (50 mg) was added to 0.4 mL of a mixed solvent of tetrahydrofuran and methyl tert-butyl ether (V:V=1:3), slurried and stirred for 90 hours at room temperature. The reaction solution was filtered, and the filter cake was collected and dried in vacuum to obtain the product (24 mg). Detected by X-ray powder diffraction, the product was present in crystal form A.

Example 24. Preparation of Crystal Form A

Crystal form B of the compound of formula (I) (25 mg) was added to 0.4 mL of a mixed solvent of ethyl acetate and n-hexane (V:V=1:1), slurried and stirred for 90 hours at room temperature. The reaction solution was filtered, and the filter cake was collected and dried in vacuum to obtain the product (18 mg). Detected by X-ray powder diffraction, the product was present in crystal form A.

Example 25. Preparation of Crystal Form A

Crystal form B of the compound of formula (I) (25 mg) was added to 0.4 mL of a mixed solvent of ethyl acetate and n-heptane (V:V=1:1), slurried and stirred for 90 hours at room temperature. The reaction solution was filtered, and the filter cake was collected and dried in vacuum to obtain the product (17 mg). Detected by X-ray powder diffraction, the product was present in crystal form A.

Example 26. Preparation of Crystal Form A

Crystal form A (20 mg) and crystal form B (20 mg) of the compound of formula (I) were added to 0.5 mL of a mixed solvent of 1,4-dioxane and water (V:V=1:2), slurried and stirred for 90 hours at room temperature. The reaction solution was filtered, and the filter cake was collected and dried in vacuum to obtain the product (25 mg). Detected by X-ray powder diffraction, the product was present in crystal form A.

Example 27. Preparation of Crystal Form A

Crystal form A (20 mg) and crystal form B (20 mg) of the compound of formula (I) were added to 0.5 mL of acetonitrile, slurried and stirred for 90 hours at room temperature. The reaction solution was filtered, and the filter cake was collected and dried in vacuum to obtain the product (18 mg). Detected by X-ray powder diffraction, the product was present in crystal form A.

Example 28. Preparation of Crystal Form A

Crystal form A of the compound of formula (I) (10 mg) was added to 1 mL of water, slurried and stirred for 18 hours at room temperature. The reaction solution was filtered, and the filter cake was collected and dried in vacuum to obtain the product (5 mg). Detected by X-ray powder diffraction, the product was present in crystal form A.

Example 29. Preparation of Crystal Form B

Amorphous crystal forms of the compound of formula (I) (200 mg) were added to 4 mL of the mixture solvent of tert-butyl acetate, methyl tert-butyl ether and n-hexane (V:V:V=1:1:2), slurried and stirred for 72 hours at room temperature. The reaction solution was filtered, and the filter cake was collected and dried in vacuum to obtain the product (80 mg). Detected by X-ray powder diffraction, the product was present in crystal form B.

Example 30. Preparation of Crystal Form B

Amorphous crystal forms of the compound of formula (I) (200 mg) were added to 0.27 mL of the mixture solvent of trifluoroethanol and isopropyl ether (V:V=2:25), warmed at room temperature to 50° C., slurried and stirred for 72 hours. The reaction solution was cooled to room temperature and filtered, and the filter cake was collected and dried in vacuum to obtain the product (18 mg). Detected by X-ray powder diffraction, the product was present in crystal form B.

Example 31. Preparation of Crystal Form B

Amorphous crystal forms of the compound of formula (I) (50 mg) were added to 0.5 mL of n-heptane, warmed at room temperature to 50° C., slurried and stirred for 72 hours. The reaction solution was cooled to room temperature and filtered, and the filter cake was collected and dried in vacuum to obtain the product (40 mg). Detected by X-ray powder diffraction, the product was present in crystal form B.

Example 32. Preparation of Crystal Form B

Amorphous crystal forms of the compound of formula (I) (50 mg) were added to 0.5 mL of the mixture solvent of chloroform and methyl tert-butyl ether (V:V=1:8), warmed at room temperature to 50° C., slurried and stirred for 72 hours. The reaction solution was cooled to room temperature and filtered, and the filter cake was collected and dried in vacuum to obtain the product (28 mg). Detected by X-ray powder diffraction, the product was present in crystal form B.

Example 33. Preparation of Crystal Form B

Crystal form A (20 mg) and crystal form B (20 mg) of the compound of formula (I) were added to 0.5 mL of a mixed solvent of ethyl acetate and n-heptane (V:V=2:3), slurried and stirred for 90 hours at room temperature. The reaction solution was filtered, and the filter cake was collected and dried in vacuum to obtain the product (28 mg). Detected by X-ray powder diffraction, the product was present in crystal form B.

Example 34. Preparation of Crystal Form B

Crystal form A (20 mg) and crystal form B (20 mg) of the compound of formula (I) were added to 0.5 mL of a mixed solvent of acetone, methyl tert-butyl ether and n-hexane (V:V:V=1:1:4), slurried and stirred for 90 hours at room temperature. The reaction solution was filtered, and the filter cake was collected and dried in vacuum to obtain the product (20 mg). Detected by X-ray powder diffraction, the product was present in crystal form B.

Example 35. Preparation of Crystal Form B

Crystal form A (20 mg) and crystal form B (20 mg) of the compound of formula (I) were added to 0.5 mL of a mixed solvent of butyl acetate, methyl tert-butyl ether and n-hexane (V:V:V=1:1:2), slurried and stirred for 90 hours at room temperature. The reaction solution was filtered, and the filter cake was collected and dried in vacuum to obtain the product (21 mg). Detected by X-ray powder diffraction, the product was present in crystal form B.

Example 36. Preparation of Crystal Form D

Crystal form B of the compound of formula (I) (1.4 g) was added to 14 mL of acetonitrile, slurried and stirred for 96 hours at room temperature. The reaction solution was filtered, and the filter cake was collected and dried in vacuum to obtain the product (1.25 g). Detected by X-ray powder diffraction, the product was present in crystal form D.

Example 37. Preparation of Crystal Form F

Amorphous crystal forms of the compound of formula (I) (30 mg) were added to 0.5 mL of the mixture solvent of 1,4-dioxane and water (V:V=1:2), slurried and stirred for 72 hours at room temperature. The reaction solution was filtered, and the filter cake was collected and dried in vacuum to obtain the product (21 mg). Detected by X-ray powder diffraction, the product was present in crystal form F.

Example 38. Preparation of Crystal Form F

Crystal form A of the compound of formula (I) (30 mg) was added to 1 mL of the mixture solvent of acetonitrile and water (V:V=1:4), slurried and stirred for 96 hours at room temperature. The reaction solution was filtered, and the filter cake was collected and dried in vacuum to obtain the product (18 mg). Detected by X-ray powder diffraction, the product was present in crystal form F.

Example 39. Preparation of Crystal Form F

Crystal form A of the compound of formula (I) (30 mg) was added to 0.8 mL of the mixture solvent of tetrahydrofuran and water (V:V=1:3) and slurried at room temperature, and the powdered solid changed into a viscous solid; the slurring was further conducted, and the viscous solid changed into a powdered solid; the slurring with stirring was conducted for a total of 96 hours. The reaction solution was filtered, and the filter cake was collected and dried in vacuum to obtain the product (16 mg). Detected by X-ray powder diffraction, the product was present in crystal form F.

Example 40. Preparation of Crystal Form F

Crystal form A of the compound of formula (I) (30 mg) was added to 1 mL of the mixture solvent of acetone and water (V:V=1:4), slurried and stirred for 96 hours at room temperature. The reaction solution was filtered, and the filter cake was collected and dried in vacuum to obtain the product (17 mg). Detected by X-ray powder diffraction, the product was present in crystal form F.

Example 41. Preparation of Crystal Form F

Crystal form A of the compound of formula (I) (40 mg) was added to 0.6 mL of the mixture solvent of isopropanol and water (V:V=1:3), slurried and stirred for 96 hours at room temperature. The reaction solution was filtered, and the filter cake was collected and dried in vacuum to obtain the product (24 mg). Detected by X-ray powder diffraction, the product was present in crystal form F.

Example 42. Preparation of Crystal Form F

Amorphous crystal forms of the compound of formula (I) (20 mg) were added to 0.3 mL of the mixture solvent of ethyl propionate and n-heptane (V:V=1:0.5), slurried and stirred for 96 hours at room temperature. The reaction solution was filtered, and the filter cake was collected and dried in vacuum to obtain the product (14 mg). Detected by X-ray powder diffraction, the product was present in crystal form F.

Example 43. Preparation of Crystal Form F

Amorphous crystal forms of the compound of formula (I) (20 mg) were added to 0.3 mL of the mixture solvent of n-propanol and isopropyl ether (V:V=1:5), slurried and stirred for 96 hours at room temperature. The reaction solution was filtered, and the filter cake was collected and dried in vacuum to obtain the product (12 mg). Detected by X-ray powder diffraction, the product was present in crystal form F.

Example 44. Preparation of Crystal Form F

Amorphous crystal forms of the compound of formula (I) (20 mg) were added to 0.3 mL of o-xylene, slurried and stirred for 96 hours at room temperature. The reaction solution was filtered, and the filter cake was collected and dried in vacuum to obtain the product (15 mg). Detected by X-ray powder diffraction, the product was present in crystal form F.

Example 45. Preparation of Crystal Form F

Amorphous crystal forms of the compound of formula (I) (20 mg) were added to 0.5 mL of the mixture solvent of 2-butanone and n-heptane (V:V=1:4), slurried and stirred for 96 hours at room temperature. The reaction solution was filtered, and the filter cake was collected and dried in vacuum to obtain the product (7 mg). Detected by X-ray powder diffraction, the product was present in crystal form F.

Example 46. Preparation of Crystal Form F

Amorphous crystal forms of the compound of formula (I) (20 mg) were added to 0.5 mL of the mixture solvent of 1,4-dioxane and isopropyl ether (V:V=1:4), slurried and stirred for 96 hours at room temperature. The reaction solution was filtered, and the filter cake was collected and dried in vacuum to obtain the product (10 mg). Detected by X-ray powder diffraction, the product was present in crystal form F.

Example 47. Preparation of Crystal Form F

Crystal form A (15 mg), crystal form D (15 mg) and crystal form F (15 mg) of the compound of formula (I) were added to 0.4 mL of n-heptane, warmed to 50° C., slurried and stirred for 120 hours. The reaction solution was cooled to room temperature and filtered, and the filter cake was collected and dried in vacuum to obtain the product (24 mg). Detected by X-ray powder diffraction, the product was present in crystal form F.

Example 48. Preparation of Crystal Form F

Crystal form A (15 mg), crystal form D (15 mg) and crystal form F (15 mg) of the compound of formula (I) were added to 0.4 mL of isopropyl ether, warmed to 50° C., slurried and stirred for 120 hours. The reaction solution was cooled to room temperature and filtered, and the filter cake was collected and dried in vacuum to obtain the product (21 mg). Detected by X-ray powder diffraction, the product was present in crystal form F.

Example 49. Preparation of Crystal Form F

Crystal form A (15 mg), crystal form D (15 mg) and crystal form F (15 mg) of the compound of formula (I) were added to 0.4 mL of a mixed solvent of chloroform and n-heptane (V:V=1:1.5), warmed to 50° C., slurried and stirred for 120 hours. The reaction solution was cooled to room temperature and filtered, and the filter cake was collected and dried in vacuum to obtain the product (20 mg). Detected by X-ray powder diffraction, the product was present in crystal form F.

Example 50. Preparation of Crystal Form F

Crystal form A (15 mg), crystal form D (15 mg) and crystal form F (15 mg) of the compound of formula (I) were added to 0.4 mL of a mixed solvent of methyl isobutyl ketone and n-heptane (V:V=1:5), warmed to 50° C., slurried and stirred for 120 hours. The reaction solution was cooled to room temperature and filtered, and the filter cake was collected and dried in vacuum to obtain the product (22 mg). Detected by X-ray powder diffraction, the product was present in crystal form F.

Example 51. Preparation of Crystal Form F

Crystal form A (10 mg), crystal form D (10 mg) and crystal form F (10 mg) of the compound of formula (I) were added to 0.5 mL of a mixed solvent of isopropanol and isopropyl ether (V:V=1:4), slurried and stirred for 96 hours at room temperature. The reaction solution was filtered, and the filter cake was collected and dried in vacuum to obtain the product (18 mg). Detected by X-ray powder diffraction, the product was present in crystal form F.

Example 52. Preparation of Crystal Form F

Crystal form A (10 mg), crystal form D (10 mg) and crystal form F (10 mg) of the compound of formula (I) were added to 0.5 mL of a mixed solvent of acetone and n-hexane (V:V=1:4), slurried and stirred for 96 hours at room temperature. The reaction solution was filtered, and the filter cake was collected and dried in vacuum to obtain the product (22 mg). Detected by X-ray powder diffraction, the product was present in crystal form F.

Example 53. Preparation of Crystal Form F

Crystal form A (10 mg), crystal form D (10 mg) and crystal form F (10 mg) of the compound of formula (I) were added to 0.5 mL of a mixed solvent of chloroform and isopropyl ether (V:V=1:4), slurried and stirred for 96 hours at room temperature. The reaction solution was filtered, and the filter cake was collected and dried in vacuum to obtain the product (21 mg). Detected by X-ray powder diffraction, the product was present in crystal form F.

Example 54. Preparation of Crystal Form F

Crystal form A (10 mg), crystal form D (10 mg) and crystal form F (10 mg) of the compound of formula (I) were added to 0.3 mL of toluene, slurried and stirred for 96 hours at room temperature. The reaction solution was filtered, and the filter cake was collected and dried in vacuum to obtain the product (26 mg). Detected by X-ray powder diffraction, the product was present in crystal form F.

Example 55. Preparation of Crystal Form F

Crystal form A (10 mg), crystal form D (10 mg) and crystal form F (10 mg) of the compound of formula (I) were added to 0.3 mL of acetonitrile, slurried and stirred for 96 hours at room temperature. The reaction solution was filtered, and the filter cake was collected and dried in vacuum to obtain the product (22 mg). Detected by X-ray powder diffraction, the product was present in crystal form F.

Example 56. Preparation of Crystal Form F

Crystal form F of the compound of formula (I) (10 mg) was added to 1 mL of water, slurried and stirred for 18 hours at room temperature. The reaction solution was filtered, and the filter cake was collected and dried in vacuum to obtain the product. Detected by X-ray powder diffraction, the product was present in crystal form F.

Example 57. Influencing Factor Experiments for Crystal Forms a, B, D and F of the Present Disclosure Crystal forms A, B, D and F of the compound of formula (I) were spread and left open to the air, and under conditions of high temperature (40° C. and 60° C.), light (4500 Lux), high humidity (RH 75% and RH 90%), the stability thereof were investigated for a period of 30 days.

Experimental Results:

TABLE 7

Results of influencing factor experiments for crystal form A and crystal form B of the compound of formula (I)

| | | Crystal form A | | | | Crystal form B | | | |
| --- | --- | --- | --- | --- | --- | --- | --- | --- | --- |
| Conditions | Time (day) | Color and trait | % Purity | % Weight gain | Crystal form | Color and trait | % Purity | % Weight gain | Crystal form |
| Initial condition | 0 | Yellow solid | 98.76 | | A | Light yellow solid | 99.65 | | B |
| 4500 Lux | 5 | Yellow solid | 98.74 | | | — | — | | |
| | 10 | Yellow solid | 98.74 | | | — | — | | |
| | 15 | — | — | | | Yellow solid | 99.01 | | |
| | 30 | Yellow solid | 98.75 | | A | Yellow solid | 98.71 | | A |
| 40° C. | 5 | Yellow solid | 98.74 | | | — | — | | |
| | 10 | Yellow solid | 98.70 | | | — | — | | |
| | 15 | — | — | | | Light yellow solid | 98.99 | | |
| | 30 | Yellow solid | 98.48 | | A | Light yellow solid | 98.57 | | A |
| 60° C. | 5 | Yellow solid | 98.73 | | | — | — | | |
| | 10 | Yellow solid | 98.68 | | | — | — | | |
| | 15 | — | — | | | Light yellow solid | 99.10 | | |
| | 30 | Yellow solid | 98.50 | | A | Light yellow solid | 98.60 | | A |
| RH 75% | 5 | Yellow solid | 98.76 | 1.15 | | — | — | — | — |
| | 10 | Yellow solid | 98.76 | 3.30 | | — | — | — | — |
| | 15 | — | — | — | | Light yellow solid | 99.62 | 6.76 | |
| | 30 | Yellow solid | 98.76 | 5.85 | A | Light yellow solid | 99.59 | 8.34 | A |
| RH 90% | 5 | Yellow solid | 98.75 | 3.18 | | — | — | — | — |
| | 10 | Yellow solid | 98.75 | 8.14 | | — | — | — | — |
| | 15 | — | — | — | | Light yellow solid | 99.64 | 14.89 | |
| | 30 | Yellow solid | 98.76 | 11.37 | A | Light yellow solid | 99.56 | 19.11 | A |

TABLE 8

Results of influencing factor experiments for crystal form D and crystal form F of the compound of formula (I)

| Conditions | Time (day) | Crystal form D | | | | Crystal form F | | | |
|---|---|---|---|---|---|---|---|---|---|
| | | Color and trait | % Purity | % Weight gain | Crystal form | Color and trait | % Purity | % Weight gain | Crystal form |
| Initial condition | 0 | Off-white solid | 99.59 | | D | | 99.67 | | F |
| 4500 Lux | 5 | Off-white solid | 99.58 | | Amorphous form | | 99.66 | | |
| | 10 | Off-white solid | 99.57 | | | | 99.64 | | |
| | 30 | Off-white solid | 99.26 | | | | 99.64 | | F |
| 40° C. | 5 | Off-white solid | 99.53 | | Amorphous form | | 99.67 | | |
| | 10 | Off-white solid | 99.02 | | | | 99.62 | | |
| | 30 | Off-white solid | 98.95 | | | | 99.57 | | F |
| 60° C. | 5 | Off-white solid | 99.40 | | Amorphous form | | 99.68 | | |
| | 10 | Off-white solid | 99.31 | | | | 99.65 | | |
| | 30 | Off-white solid | 99.09 | | | | 99.59 | | F |
| RH 75% | 5 | Off-white solid | 99.56 | 5.30 | Amorphous form | | 99.65 | 5.23 | |
| | 10 | Off-white solid | 99.53 | 5.48 | | | 99.63 | 5.34 | |
| | 30 | Off-white solid | 99.55 | 5.56 | | | 99.62 | 10.03 | F |
| RH 90% | 5 | Off-white solid | 99.57 | 7.45 | Amorphous form | | 99.66 | 7.26 | |
| | 10 | Off-white solid | 99.54 | 8.67 | | | 99.63 | 8.40 | |
| | 30 | Off-white solid | 99.55 | 9.53 | | | 99.65 | 12.83 | F |

Experiment Conclusion:

It is shown in the results of influencing factor experiments in tables 7 and 8 that after placed under the conditions of light, high temperature of 40° C., high temperature of 60° C., high humidity of 75% RH or high humidity of 90% RH for 30 days, crystal form A and crystal form F exhibit a good physical and chemical stability.

Example 58. Long-Term Accelerated Stability Experiments for Crystal Form A and Crystal Form F of the Present Disclosure The long-term (25° C., 60% RH) and accelerated (40° C., 75% RH) stability of crystal form A and crystal form F of the compound of formula (I) were investigated for 3 months.

Experimental Results:

TABLE 9

Results of long-term accelerated stability experiments for crystal form A and crystal form F of the compound of formula (I):

| Sample | Placement condition | Initial condition | % Purity 1 month | % Purity 2 months | % Purity 3 months | Crystal form |
|---|---|---|---|---|---|---|
| Crystal form A | 25° C., 60% RH | 98.79 | 98.80 | 98.77 | 98.76 | A |
| | 40° C., 75% RH | 98.79 | 98.79 | 98.75 | 98.74 | A |
| Crystal form F | 25° C., 60% RH | 99.69 | 99.68 | 99.65 | 99.65 | F |
| | 40° C., 75% RH | 99.69 | 99.68 | 99.67 | 99.66 | F |

It is shown in the results of long-term accelerated stability experiments in table 9 that after placed under long-term (25° C., 60% RH) and accelerated (40° C., 75% RH) conditions for 3 months, crystal form A and crystal form F exhibit a good physical and chemical stability.

Although the specific embodiments of the present disclosure have been described above, it will be understood by those skilled in the art that these are merely illustrative, and that various alterations or modifications can be made to these embodiments without departing from the principle and essence of the present disclosure. Therefore, the scope of protection of the present disclosure is defined by the appended claims.

What is claimed is:

1. Crystal form A, B, C, D, E, or F of a compound of formula (I), (S)-4-(4-(tert-butoxy)-2-(4-(5-chloro-2-propionylphenyl)-5-methoxy-2-oxopyridin-1(2H)-yl)butanamido) benzoic acid, wherein:

the crystal form A has an X-ray powder diffraction pattern comprising characteristic peaks at 2θ of 7.420, 8.000, 8.642, 12.900 and 22.400; the crystal form B has an X-ray powder diffraction pattern comprising characteristic peaks at 2θ of 7.620, 8.680, 11.042, 11.638, 12.339, 16.320 and 19.381; the crystal form C has an X-ray powder diffraction pattern comprising characteristic peaks at 2θ of 7.283, 8.780, 10.664, 11.264, 14.744, 15.456, 16.587 and 17.598; the crystal form D has an X-ray powder diffraction pattern comprising characteristic peaks at 2θ of 7.021, 7.901, 8.259, 9.200, 10.639, 12.320, 13.821, 14.180, 14.580, 15.519, 16.120, 16.661, 18.500, 19.919 and 20.600; the crystal form E has an X-ray powder diffraction pattern comprising characteristic peaks at 2θ of 6.460, 7.480, 7.977, 16.220, 19.360 and 21.720; the crystal form F has an X-ray powder diffraction pattern comprising characteristic peaks at 2θ of 5.761, 9.800, 10.640, 11.621, 14.021, 16.180, 16.460, 17.520, 21.460 and 24.580, Compound of formula (I)

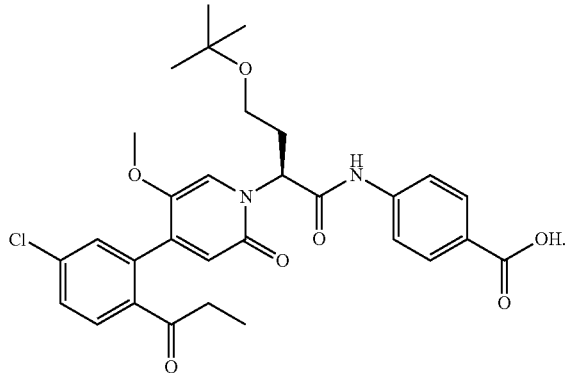

2. The crystal form as defined in claim 1, wherein the crystal form is crystal form A, wherein the crystal form has an X-ray powder diffraction pattern comprising characteristic peaks at 2θ of 7.420, 8.000, 8.642, 12.900, 16.281, 18.280, 20.018, 21.119, 22.400, 24.458 and 26.100.

3. The crystal form as defined in claim 1, wherein the crystal form is crystal form B.

4. The crystal form as defined in claim 1, wherein the crystal form is crystal form C.

5. The crystal form as defined in claim 1, wherein the crystal form is crystal form D.

6. The crystal form as defined in claim 1, wherein the crystal form is crystal form E.

7. The crystal form as defined in claim 1, wherein the crystal form is crystal form F.

8. The crystal form as defined in claim 7, wherein the crystal form has an X-ray powder diffraction pattern comprising characteristic peaks at 2θ of 5.761, 9.800, 10.640, 11.621, 14.021, 16.180, 16.460, 16.740, 17.520, 21.460, 22.820, 23.939, 24.580 and 26.280.

9. The crystal form as defined in claim 7, wherein the crystal form has an X-ray powder diffraction pattern comprising characteristic peaks at 2θ of 5.761, 9.800, 10.640, 11.621, 14.021, 16.180, 16.460, 16.740, 17.520, 18.560, 19.142, 19.820, 21.460, 22.820, 23.939, 24.580, 25.981, 26.280, 26.861, 27.700, 28.580, 28.921, 29.480, 30.840, 31.340, 32.801, 33.300, 33.921, 35.321, 36.843, 38.660, 40.101, 41.121 and 41.600.

10. A method for preparing crystal form A, B, C, D, E or F of the compound of formula (I), (S)-4-(4-(tert-butoxy)-2-(4-(5-chloro-2-propionylphenyl)-5-methoxy-2-oxopyridin-1(2H)-yl)butanamido)benzoic acid, as defined in claim 1, comprising: taking an amount of the compound of formula (I), adding an appropriate amount of a solvent for crystallization, filtering and drying to obtain crystal form A, crystal form B, crystal form C, crystal form D, crystal form E or crystal form F of the compound of formula (I).

11. The crystal form as defined in claim 1, wherein the crystal form has an error range of 2θ values of ±0.2.

12. A pharmaceutical composition, wherein the pharmaceutical composition comprises the crystal form as defined in claim 1 and further comprises one or more pharmaceutically acceptable carriers, diluents or excipients.

13. A method for preparing a pharmaceutical composition, wherein the method comprises mixing the crystal forms as defined in claim 1 with at least one pharmaceutically acceptable carrier, diluent or excipient.

14. A method for treating cardiovascular and cerebrovascular diseases, comprising administering to a subject in need thereof an effective amount of a pharmaceutical composition comprising the crystal form as defined in claim 1, wherein the cardiovascular and cerebrovascular diseases are selected from thromboembolic diseases, myocardial infarction, angina, reocclusion and restenosis after angioplasty or aortic coronary artery bypass, disseminated intravascular coagulation, stroke, transient ischemia attack, peripheral arterial occlusive diseases, pulmonary embolism or deep vein thrombosis.

* * * * *